United States Patent
Poulsen et al.

(10) Patent No.: US 10,583,313 B2
(45) Date of Patent: Mar. 10, 2020

(54) MITIGATION OF INTERPLAY EFFECT IN PARTICLE RADIATION THERAPY

(71) Applicants: Varian Medical Systems Particle Therapy GmbH, Troisdorf (DE); University of Maryland, Baltimore, Baltimore, MD (US)

(72) Inventors: Per Rugaard Poulsen, Abyhoj (DK); John Eley, Baltimore, MD (US); Ulrich Langner, Ellicott City, MD (US); Katja Langen, Baltimore, MD (US)

(73) Assignees: Varian Medical Systems Particle Therapy GmbH, Troisdorf (DE); University of Maryland, Baltimore, Baltimore, MD (US)

(*) Notice: Subject to any disclaimer, the term of this patent is extended or adjusted under 35 U.S.C. 154(b) by 190 days.

(21) Appl. No.: 15/908,334

(22) Filed: Feb. 28, 2018

(65) Prior Publication Data

US 2018/0280729 A1    Oct. 4, 2018

(51) Int. Cl.
*A61N 5/10* (2006.01)
*A61N 5/00* (2006.01)

(52) U.S. Cl.
CPC ........... *A61N 5/1067* (2013.01); *A61N 5/00* (2013.01); *A61N 5/1037* (2013.01); *A61N 5/1039* (2013.01); *A61N 5/1043* (2013.01); *A61N 5/1044* (2013.01); *A61N 5/1075* (2013.01); *A61N 2005/1087* (2013.01); *A61N 2005/1089* (2013.01)

(58) Field of Classification Search
None
See application file for complete search history.

(56) References Cited

U.S. PATENT DOCUMENTS

| | | | |
|---|---|---|---|
| 2013/0303899 A1 | 11/2013 | Mistry et al. | |
| 2014/0031602 A1 | 1/2014 | Fujimoto et al. | |
| 2016/0030769 A1* | 2/2016 | Cameron | A61N 5/1043 600/1 |
| 2017/0157422 A1* | 6/2017 | Zwart | A61N 5/1044 |
| 2017/0203129 A1* | 7/2017 | Dessy | A61N 5/1075 |
| 2018/0020535 A1* | 1/2018 | Cooley | A61N 5/103 |

OTHER PUBLICATIONS

Tsunashima, Yoshikazu, "Verification of the Clinical Implementation of the Respitory Gated Beam Delivery Technique with Synchrotron-based Proton Irradiation", UT GSBS Dissertations and Theses(Open Access), 2012.

* cited by examiner

*Primary Examiner* — Hoon K Song

(57) ABSTRACT

The present disclosure relates to a new scan technique for particle radiation therapy that may be used for cancer treatment. One embodiment relates to a method of mitigating interplay effect in particle radiation therapy in a moving target including a period of movement, where the particle radiation therapy defines a planned dose in each spot of each layer of the moving target. The method comprising dividing the planned dose in each spot into a number of spot repaintings; and generating a scan pattern for each layer by defining a beam-on time at each spot for each spot repainting, and calculating a wait time between consecutive beam-on times to distribute the spot repaintings for each spot of a respective layer are distributed over a duration of an integer number of periods of movement.

21 Claims, 28 Drawing Sheets

$$t_{wait} = \begin{cases} 0, & \text{if } \Delta x < d_{threshold} \text{ and } \Delta y < d_{threshold} \\ \max\left(t_{0,x} + \frac{\Delta x}{V_x}, t_{0,y} + \frac{\Delta y}{V_y}\right), & \text{otherwise} \end{cases} \quad (1)$$

$$t_{beam-on} = MU \cdot \left(\frac{t_{min}}{MU_{min\_layer}}\right) \quad (2)$$

$$t_{min} = \begin{cases} 1.94 \text{ ms}, & \text{if } MU_{min\_layer} > MU_{min} \\ 1.62 \text{ ms}, & \text{if } MU_{min\_layer} = MU_{min} \text{ and energy} < 149 \text{ MeV} \\ 2.13 \text{ ms}, & \text{if } MU_{min\_layer} = MU_{min} \text{ and energy} \geq 149 \text{ MeV} \end{cases} \quad (3)$$

FIG. 2B

Summary of 8 Scan Modes with Increasing Layer Durations

| | Scan mode | Scan direction | Scan path | Repaintings (n) | Layers, (%) | MUs (%) |
|---|---|---|---|---|---|---|
| fastest | 1 | Y | Sequential | Even, maximum 16 | 50 (21.1) | 56.7 |
| | 2 | X | Sequential | Even, maximum 16 | 23 (9.7) | 10.1 |
| | 3 | Y | First odd, then even spots | Even, maximum 16 | 9 (3.8) | 4.8 |
| | 4 | X | First odd, then even spots | Even, maximum 16 | 9 (3.8) | 3.6 |
| | 5 | Y | Increased spot jumps | Even, maximum 16 | 13 (5.8) | 4.1 |
| | 6 | X | Increased spot jumps | Even, maximum 16 | 1 (0.4) | 0.2 |
| | 7 | X | Increased spot jumps | Even, no limit | 48 (20.3) | 11.8 |
| | 8a (4s) | X | Increased spot jumps | Any | 11 (4.6) | 2.3 |
| slowest | 8b (<4 s) | X | Increased spot jumps | Any | 73 (33.8) | 6.5 |

*Abbreviation:* MU = monitor units.
Scan modes shown in order of increasing layer duration: scan modes 8a and 8b are identical, except that mode 8b denotes layer duraitons <4 seconds.

*FIG. 7*

| Delivery Scheme | Experiments $\gamma_{exp}$ (3%/3mm) | Simulations of experiments $\gamma_{sim}$ (3%/3mm) | Simulations with 10 different start phases $\gamma_{sim}$ (3%/3mm) |
|---|---|---|---|
| Default | 59.6% ± 9.7% | 59.2% ± 9.6% | 59.8% ± 8.4% |
| 8 repaintings | 76.5% ± 10.8% | 76.4% ± 11.1% | 79.1% ± 10.2% |
| Optimized | 92.4% ± 3.8% | 92.8% ± 4.0% | 92.5% ± 4.4% |
| | n = 24 | n = 24 | n = 240 |

FIG. 17

MITIGATION OF INTERPLAY EFFECT IN PARTICLE RADIATION THERAPY

CROSS-REFERENCE TO RELATED APPLICATIONS

This application claims the benefit of and priority to U.S. Provisional Application No. 62/445,008, filed on Jan. 11, 2017, which is hereby incorporated by reference in its entirety.

FIELD

Embodiments relate to particle radiation therapy. More specifically, embodiments relate to scan techniques to mitigate interplay effect in delivery of particle radiation to a treatment target in motion.

BACKGROUND

Particle radiation therapy (also called hadron therapy) is a form of external beam radiotherapy that uses beam(s) of energetic protons, ions, electrons, or electrons for treatment of cancer or other diseases. Further, pencil beam scanning (PBS) therapy is a type of particle radiation therapy that often allows excellent three-dimensional (3D) shaping of a high-dose radiation volume to a shape of a treatment target such as a tumor. With particle PBS therapy, the radiation treatment is delivered in several layers (beam energies or energy layers), where a pencil beam of energized particles is scanned to cover a cross section of the treatment target at specific energy-dependent depths.

However, during particle PBS therapy delivery, treatment target motion (e.g., tumor motion), for example, due to breathing or the heartbeat, will change the relative positions of treatment target volumes or spots that are irradiated sequentially by the scanning pencil beam. The size of the treatment target volumes or spots depends on a width of the pencil beam of energized particles. The resulting redistribution of dose in the treatment target tissue is called the interplay effect, and it can lead to severe local underdosage and/or overdosage inside the treatment target volume. This is a major concern for particle PBS therapy in the thorax and abdomen, in particular for stereotactic body radiotherapy (SBRT), where high doses are delivered in few fractions. Besides the interplay effect, treatment target motion (e.g., tumor motion) also shifts and smears the delivered target dose, but this smearing effect is common for particle PBS therapy and other treatment techniques, such as conventional photon radiotherapy and passively scattered particle beams. Unlike other motion-induced dose perturbations that impact the dose at the treatment target edge (e.g., dose blurring due to random position errors and dose shifts due to systematic position errors), the interplay effect typically cannot be accounted for by a simple expansion of the high-dose radiation volume with safety margins.

Although the interplay effect may tend to average out after several treatment deliveries because the hot spot and cold spot locations typically differ randomly between each treatment delivery, the interplay effect is more serious for treatments delivered in few fractions because the dose smearing effect of many fractions is absent. Since SBRT is delivered in few fractions, SBRT is susceptible to pronounced interplay effect in moving target organs, such as lung, liver, or pancreas. Consequently, many particle radiation therapy centers do not offer SBRT treatments at all. Even for normal-fractionated treatments, many particle radiation therapy centers only treat highly selected tumors with minor motion due to respiratory motion.

SUMMARY

A new scan technique that integrates repainting for particle radiation therapy to efficiently reduce interplay effects is disclosed. The new scan technique is suitable for mitigating interplay effects in particle radiation therapy delivered to a moving treatment target, such as a tumor. In embodiments, the motion of the moving treatment target is periodic and has a period, where the period may be determined in any manner, such as experimental, empirical, or calculation methods. Moreover, the motion may be due to respiration, heartbeat, or other motion source.

In cross-sectional layers of the treatment target, a spot or region is irradiated with the particle radiation according to the new scan technique. A particle radiation treatment plan typically defines a planned dose at each spot of each layer of the treatment target. A shape of the spot may be any of numerous shapes, may have multiple-dimensions (e.g., two-dimensional 2D or three-dimensional 3D), and may have a volume. Continuing, the spot may have a wait time that corresponds to time between beam-on times at the spot and a bean-on time that corresponds to time during which the bean of particle radiation irradiates the spot. Additionally, the wait time may correspond to time before a first beam irradiates the spot. The new scan technique focuses on optimizing the wait time to achieve reduction in the interplay effect. In contrast, conventional methods of addressing the interplay effect optimize the beam-on time.

According to embodiments, a planned dose for a spot of a layer is divided into a number of spot repaintings. Similar action is performed for the rest of the spots of the layer. Also, a scan pattern for each layer is generated by defining a beam-on time at each spot for each spot repainting and calculating a wait time between consecutive beam-on times at each spot. The wait time is calculated such that the spot repaintings for each spot of the layer are distributed over an integer number of periods of movement of the moving treatment target. In an embodiment, the spot repaintings are distributed evenly within the integer number of periods. The treatment delivery at each spot may be defined by the waiting time (for layer shift or spot position shift) followed by the beam-on time. Moreover, the scan pattern generation may be seen as determining an order of the spot repaintings. In an example, the period of movement may be the breathing period/cycle of a patient under radiation treatment. The breathing period is typically quite stable. Additionally, the period of movement also may be an approximate period of an approximately periodic movement.

Accordingly, the interplay effect in each individual layer (or energy layer) may be smeared out by tuning a duration of layer treatment delivery to one or more periods of movement. Further, the dose delivered to each spot in the layer may be delivered in equal portions with equal temporal separations over duration of the period of movement. This ensures that the mean shift of each spot relative to its planned position is close to zero, which in turn gives a large reduction of the interplay effect. Also, it possible to use a different number of repaintings for each spot, but still spread out the spot repaintings throughout the period of movement.

Therefore, the new scan technique spreads the treatment delivery of each energy layer over the period of movement (e.g., a breathing cycle), allows spot-specific numbers of spot repaintings, and ensures that the spot repaintings are spread over the duration of the movement period. Mitigation of the interplay effect in particle radiation therapy by using the new scan technique is superior to conventional methods of mitigating the interplay effect. Moreover, the new scan technique allows safe PBS treatments of tumors undergoing respiratory motion in the thorax or abdomen, including SBRT treatments delivered in very few fractions. In an embodiment, no monitoring of the patient's breathing or synchronization of the treatment delivery to the breathing phase is needed. Further, the new scan technique may be immediately implemented at existing particle radiation therapy centers such as cyclotron-based proton radiation therapy facilities without any requirements of intra-treatment motion monitoring, gating, or synchronization between patient breathing and treatment delivery. In an embodiment, the new scan technique involves configuring the spot treatment delivery sequence in a Digital Imaging and Communications in Medicine (DICOM) proton radiation treatment plan.

BRIEF DESCRIPTION OF THE DRAWINGS

The accompanying drawings, which are incorporated in and form a part of this specification, illustrate embodiments, together with the description, serve to explain the principles of the disclosure.

FIG. 2B illustrates equations for waiting time $t_{wait}$, beam-on time $t_{beam-on}$, and $t_{min}$ related to a spot according to an embodiment.

FIG. 7 shows a table with eight scan modes in order of increasingly slower scan duration according to an embodiment.

FIG. 17 illustrates the results for 3×24 motion experiments according to an embodiment.

DETAILED DESCRIPTION

Figure 1A:
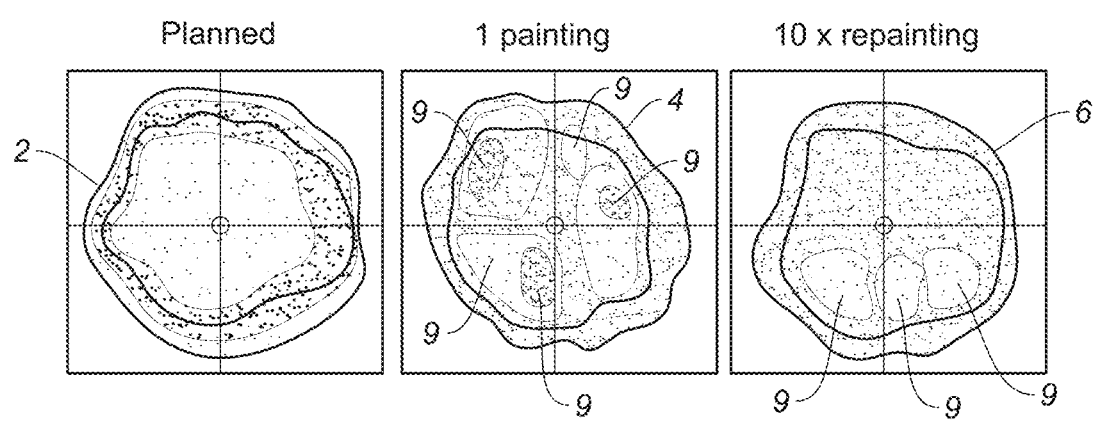
FIG. 1A illustrates three dose distributions with proton PBS to liver tumors.

Reference will now be made in detail to embodiments, examples of which are illustrated in the accompanying drawings. While the disclosure will be described in conjunction with these embodiments, it should be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description, numerous specific details are set forth in order to provide a thorough understanding. However, it will be recognized by one of ordinary skill in the art that embodiments may be practiced without these specific details.

Although the description will focus on proton radiation therapy and proton pencil beam scanning (PBS) therapy, the description is also applicable to particle radiation therapy that uses neutrons, ions, or electrons. The proton radiation therapy may irradiate a treatment target of a patient. The treatment target may comprise a tumor, diseased tissue, or at least part thereof. In embodiments, a motion of the treatment target is periodic and has a period. For example, the motion may be due to a periodic movement of a breathing cycle or a heartbeat. Alternatively, the motion of the treatment target may be approximately periodic and may have an approximate period. The period of movement such as the breathing period and/or heartbeat movement may be obtained from a 4D Computed Tomography scan (4DCT), which may be performed for radiation treatment planning. In an embodiment, auditory and/or visual guidance may be utilized during treatment delivery to assist the patient to breathe with the period duration (or the frequency) recorded during the 4DCT scan session.

Continuing, a dose delivered to a spot has a value that is at least a predefined minimum dose dependent on particle radiation therapy equipment delivering the dose. In order to mitigate the interplay effect, the number of spot repaintings at each spot is maximized or optimized according to the predefined minimum dose (or minimum spot dose) of the particle radiation therapy. The spot repaintings of each spot of a layer may then be distributed over an integer number of periods of movement. In an embodiment, the spot repaintings are distributed evenly over the duration of the integer number of periods. Because the particle radiation therapy equipment typically is limited to the predefined minimum dose, some spots of the treatment target will be irradiated once instead of being irradiated multiple times. According to the new scan technique, a scan pattern may then be generated such that spots in a layer that are irradiated once are distributed in a manner in which one set of these spots is irradiated during a first part of the period of the periodic motion and the other set of these spots is irradiated during a second part of the period of the periodic motion.

In embodiments, layers with a maximum scan time less than the period of the periodic motion may be scanned using a scan pattern with a maximum scan time. Also, spot repaintings in a scan pattern for a layer may be distributed by adjusting a sequence order of spots and/or spot repaintings in the layer and/or by adjusting the wait time between consecutive beam-on times of spots in the layer. In some particle radiation therapy facilities, it is not possible to pause the beam of energized particles with 100% controllability. The new scan technique avoids this problem by focusing on adjusting the wait time of spots, the sequence of spot repaintings, and the number of spot repaintings to distribute the radiation delivery of the therapy. But, it may be an option to be able to pause the beam of energized particles in some particle radiation therapy facilities. In further embodiments, the wait time between consecutive beam-on times of a spot in a layer may therefore be adjusted by selecting a beam pause before one or more spots in a scan pattern.

The number of spot repaintings for each spot of a layer may be decomposed into repainting blocks or groups, where the number of spot repaintings in each repainting block (or group) may be an integer power of two, in an embodiment. Accordingly, the spot repaintings of each repainting block may be distributed over an integer number of periods of movement in an embodiment. The spot repaintings may be distributed evenly over the duration of the integer number of periods of movement. Also, synchronization of a patient's breathing and a determined respiratory period of movement may be assisted by means of audio and/or visual guidance.

Continuing, in cases where the scan time for a layer is two periods, the scan pattern may be generated such that repainting blocks of two or more spot repaintings are separated into two identical scan patterns, where a first scan pattern is performed in the first period of two periods and a second scan pattern is performed in the second period of two periods. Alternatively, the scan pattern may be generated such that repainting blocks of two or more spot repaintings are separated into two scan patterns, where a first scan pattern is performed in a first period of two periods and a second scan is performed in a second period of two periods, the second scan pattern being the reverse of the first scan pattern.

Modeling of Proton PBS Timing

An ideal dose distribution to a moving tumor without interplay effects (although with smearing) would be the planned dose to the static tumor smeared or convolved with the tumor motion. This may to some degree be obtained by repainting (or rescanning), where the beam of energized particles is scanned several times over spots of a treatment target to smear out the interplay effect. The beam of energized particles may be scanned N times over spots of the treatment target (N=2, 3, 4,), each time delivering 1/N of the planned dose (or monitor units) to each spot. The number of monitor units (MU) cannot be smaller than a minimum limit $MU_{min}$. A typical clinical proton PBS treatment plan may have many spots with too few MUs to allow any repainting at all. Further, conventional methods of reducing the interplay effect are inefficient. They do not guarantee elimination of the interplay effect. Also, they are often not practically applicable because of proton radiation therapy equipment limitations imposed by proton accelerators and their beams of energized protons.

The new scan technique is superior to conventional strategies for mitigating the interplay effect in proton PBS therapy according to experiments, simulations, and dose reconstructions, as will be described next. In the discussion below, motion of the treatment target is due to periodic respiratory movement with a breathing period T=4 s. It should be understood that the discussion is equally applicable to other types of periodic movement and to other values for the period.

FIG. 1A illustrates three dose distributions with proton PBS to liver tumors. Dose distribution 2 shows a planned uniform dose distribution with proton PBS to a motionless liver tumor. Dose distribution 4 depicts delivered doses in simulated treatments without repainting (1 painting or spots painted once) with proton PBS to a moving liver tumor. Further, dose distribution 6 depicts delivered doses in simulated treatments with 10× repainting (spots painted 10 times) with proton PBS to a moving liver tumor.

The interplay effect between liver tumor motion and the scanning proton beam leads to severe underdoses/overdoses 9 in the dose distribution 4. This interplay effect is to some degree smeared out by the 10 repaintings in the dose distribution 6 to cause a reduction in underdoses/overdoses 9, but it is still a problem.

Figure 1B:
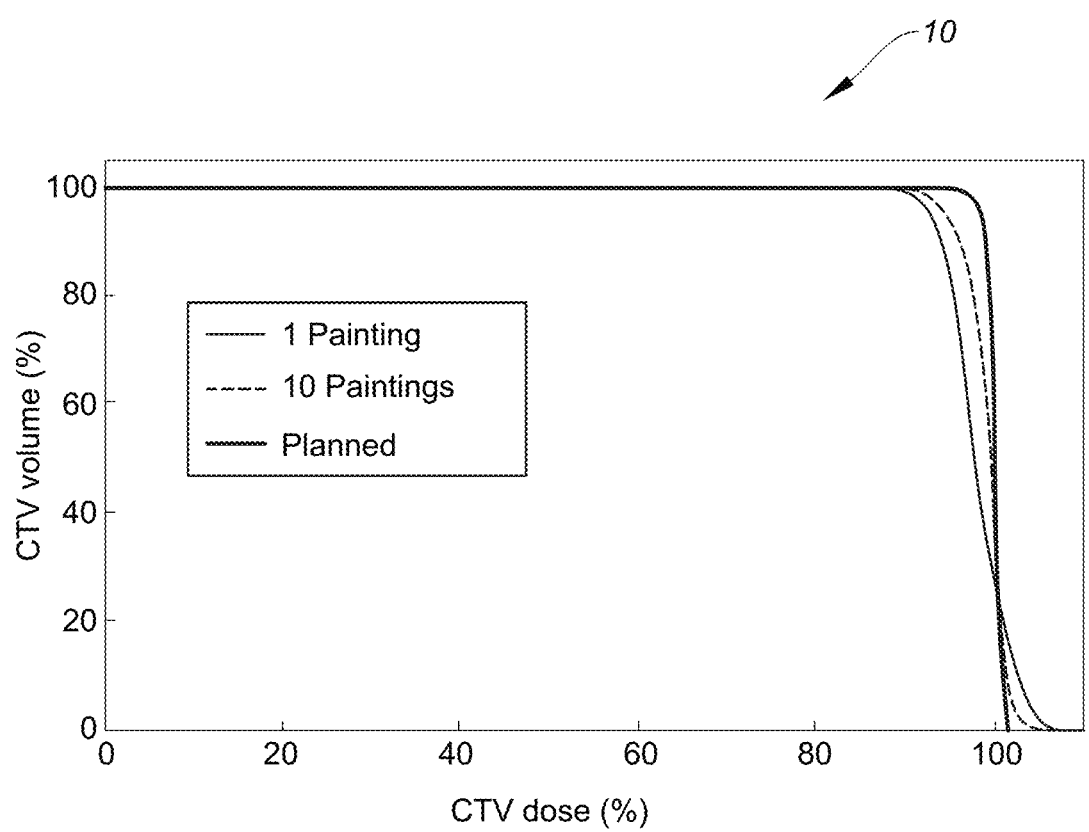
FIG. 1B depicts a dose-volume histogram for the liver tumors of FIG. 1A.

FIG. 1B depicts a dose-volume histogram 10 for the liver tumors of FIG. 1A. The dose-volume histogram 10 points out the underdoses/overdoses 9 in the dose distributions 4 and 6.

As mentioned above, motion of the treatment target is due to periodic respiratory movement with a breathing period T=4 s. It should be understood that the discussion is equally applicable to other types of periodic movement and to other values for the period.

For the new scan technique, modeling of the timing of treatment delivery to spots of a layer permits adjustment of duration of treatment deliver to the layer to be an integer number of periods, where the period T=4 s for this discussion.

Figure 2A:
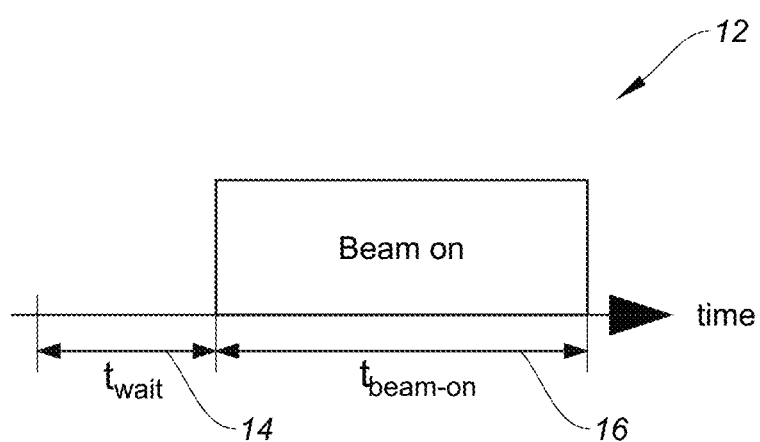
FIG. 2A shows a timing graph of treatment delivery to a spot in a layer according to an embodiment.

Continuing, FIG. 2A shows a timing graph 12 of treatment delivery to a spot in a layer according to an embodiment. According to the timing graph 12, the spot has a waiting time $t_{wait}$ 14 (for layer shift or spot position shift) followed by a beam-on time $t_{beam-on}$ 16.

For proton PBS therapy equipment of a proton radiation therapy center, patient treatment log files may be analyzed to find an approximate value for the waiting time $t_{wait}$ 14. Equation (1) of FIG. 2B was derived from the patient treatment log files for the waiting time $t_{wait}$ 14. The equation (1) for the waiting time $t_{wait}$ 14 includes the following values: the spot delay constants $t_{0,x}$=2.85 ms and $t_{0,y}$=3.52 ms and spot speeds $v_x$=6.92 mm/ms in the X-direction and $v_y$=32.1 mm/ms in the Y-direction. The threshold distance $d_{threshold}$ between spots is 10 mm. Also, the waiting time $t_{wait}$ 14 depends on the distance ($\Delta x$ and $\Delta y$) of the spot from the previous spot. The spot speeds $v_x$ and $v_y$ depend approximately linearly on the proton beam energy, but this is omitted in the modeling of the waiting time $t_{wait}$ 14. Although the modeling of the waiting time $t_{wait}$ 14 may be improved, it is found to be sufficiently accurate to demonstrate the advantages of the new scan technique to reduce the interplay effect.

Additionally, equation (2) of FIG. 2B was derived from the patient treatment log files for the beam-on time $t_{beam\text{-}on}$ 16. According to equation (2), the beam-on time $t_{beam\text{-}on}$ 16 of a spot is proportional to the dose or number of monitor units (MU) delivered to the spot. Here, $MU_{min\_layer}$ is the minimum number of MUs in any spot in the layer, and $t_{min}$ is the beam-on time for spots with $MU=MU_{min\_layer}$, which corresponds to the shortest beam-on time in the layer. Also, FIG. 2B's equation (3) for $t_{min}$ represents approximate and empirically determined values for $t_{min}$.

Figure 3:
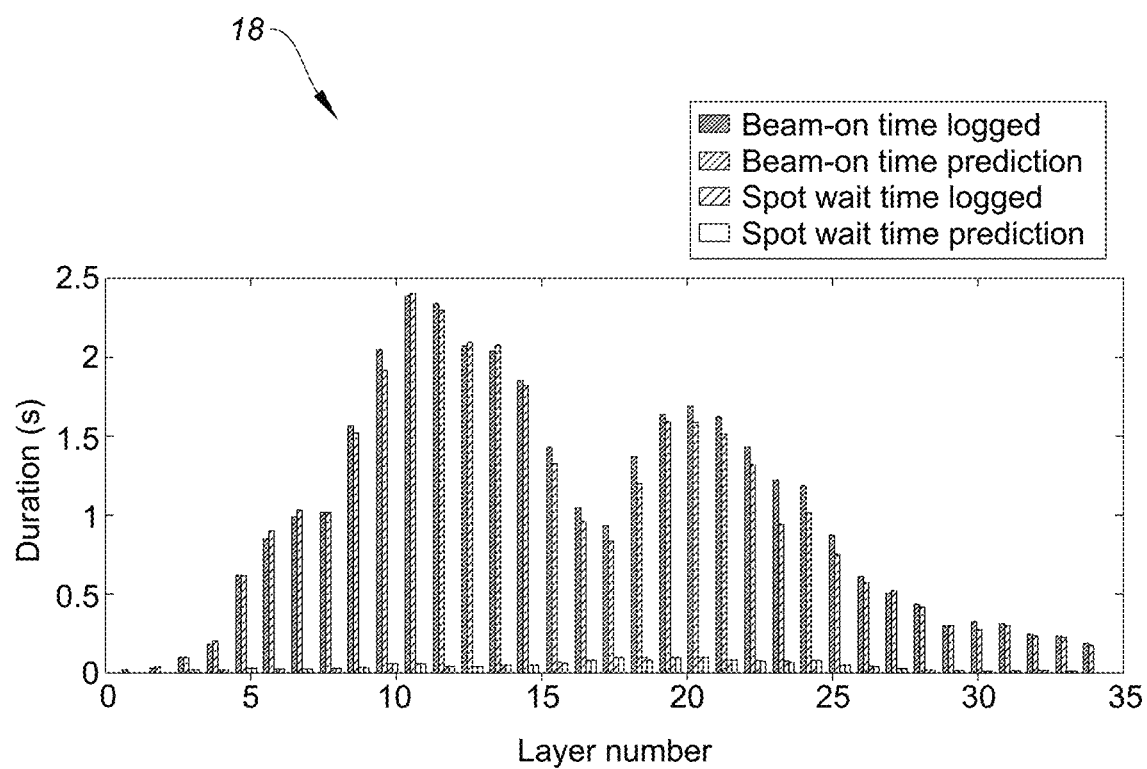
FIG. 3 depicts a comparison graph of actual times with predicted times from equations (1)-(3) according to an embodiment.
Figure 4:
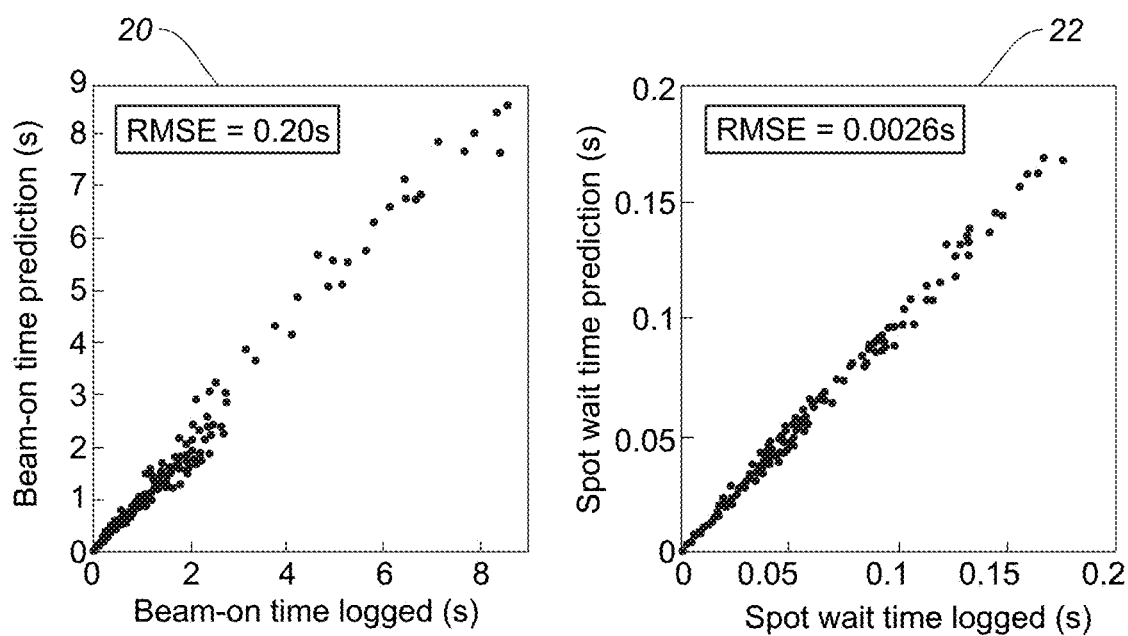
FIG. 4 shows scatter plots of actual and predicted values of $t_{wait}$ and $t_{beam-on}$ according to an embodiment.

FIG. 3 depicts a comparison graph 18 of actual beam-on times $t_{beam\text{-}on}$ and beam waiting times $t_{wait}$ for 35 energy layers of a proton field with the beam-on times $t_{beam\text{-}on}$ and beam waiting times $t_{wait}$ as predicted from equations (1)-(3) according to an embodiment. The actual times are in agreement with the predicted times of equations (1)-(3), demonstrating the accuracy of equations (1)-(3). Further, FIG. 4 shows scatter plots 20 and 22 of actual and predicted values of $t_{wait}$ and $t_{beam\text{-}on}$ for all energy layers in 13 investigated clinical treatment fields according to an embodiment. As shown in FIG. 4, equations (1)-(3) in general give a reasonably accurate prediction of beam-on time $t_{beam\text{-}on}$ and waiting time $t_{wait}$. Also, the root-mean-square error in the predicted times are 0.20 s and 0.0026 s for predicted beam-on time $t_{beam\text{-}on}$ and waiting time $t_{wait}$, respectively.

New Scan Technique that Integrates Repainting

The new scan technique provides the ability to adjust the treatment delivery time of each energy layer to a period of movement (e.g., the breathing period of a patient). As mentioned above, the period of movement is assumed to be a breathing cycle of 4 seconds. It should be understood that the discussion is equally applicable to different types of periodic movement and different values for the period.

Conventional methods have tried to manipulate the treatment delivery time of a layer by adjusting the beam current, which is equivalent to adjusting the beam-on time $I_{beam\text{-}on}$. However, this strategy has very limited flexibility. It only allows modest prolongation of the treatment delivery time of the layer since most energy layers already are delivered with the lowest allowed beam current for the layer.

Figure 5:
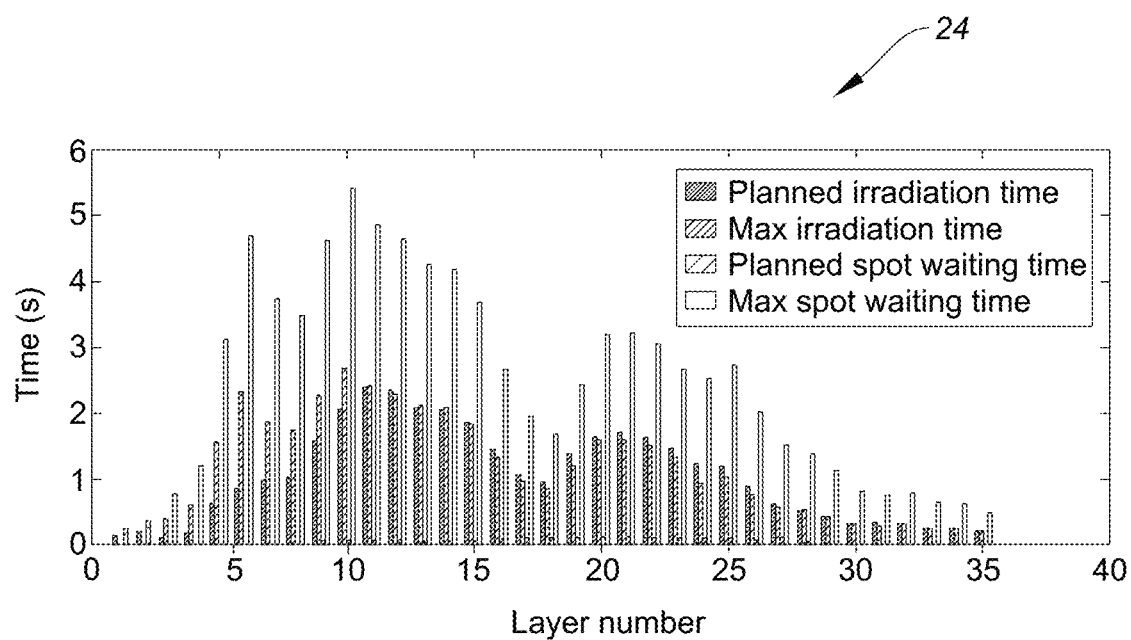
FIG. 5 depicts a graph of maximum and planned waiting times $t_{wait}$ and beam-on times $t_{beam-on}$ of spots in a layer according to an embodiment.

Instead, the new scan technique manipulates the time between each spot, which represents the waiting time $t_{wait}$ 14 defined in FIG. 2A. FIG. 5 depicts a graph 24 of maximum and planned waiting times $t_{wait}$ and beam-on times $t_{beam\text{-}on}$ (or irradiation time) of spots in a layer according to an embodiment. As seen in FIG. 5, the maximum waiting times $t_{wait}$ of spots in the layer may be extended significantly more relative to the maximum beam-on times $t_{beam\text{-}on}$ (or irradiation time) of spots of the layer. This allows extension of the treatment delivery duration of many energy layers to the period T=4 s or more. Further, the graph 24 shows time values for 35 energy layers. Maximum waiting times $t_{wait}$ may be obtained by maximizing the waiting time between spots of the layer while maximum beam-on times $t_{beam\text{-}on}$ may be obtained by decreasing beam current to its minimum.

The new scan technique ensures temporal equidistant repaintings of each spot of a layer throughout the period T=4 s of the breathing cycle in an embodiment. Implementation of the new scan technique is described next.

Figure 6:
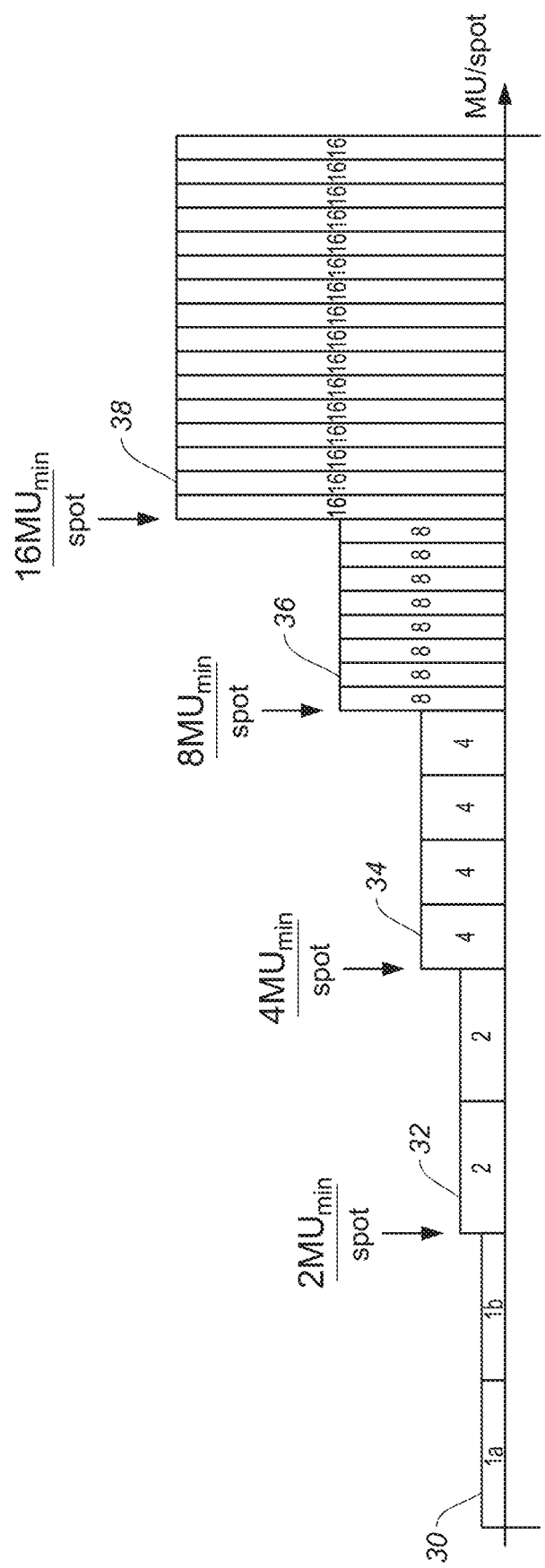
FIG. 6 illustrates spots sorted into repainting blocks according to an embodiment.

Initially, spots of a layer are sorted according to how many times the spots may be repainted. Specifically, the spots are sorted into repainting blocks (or groups) 30, 32, 34, 36, and 38 as illustrated in FIG. 6 according to an embodiment. Depending on the number of MUs to be delivered of the spots, the layer's spots are sorted into repainting blocks 32, 34, 36, and 38 for the spots to be painted 2, 4, 8, and 16 times, respectively. $MU_{min}$ is predefined and represents a minimum allowed number of MUs for a spot. Accordingly, spots with $>=16\ MU_{min}$ are put into 16-paint repainting blocks 38. Spots with $>=8MU_{min}$ are put into 8-paint repainting blocks 36. Spots with $>=4MU_{min}$ are put into 4-paint repainting blocks 34. Spots with $>=2MU_{min}$ are put into 2-paint repainting blocks 32. Spots with $<2\ MU_{min}$ are put into one of the 1-paint repainting blocks 30. Further, a spot may be placed in more than one of repainting blocks (or groups) 32, 34, 36, and 38. For example, a spot with 14 $MU_{min}$ will be placed in the 8-paint repainting blocks 36, the 4-paint repainting blocks 34, and the 2-paint repainting blocks 32 because 14=8+4+2.

Moreover, the two 2-paint repainting blocks 32 are identical. They include the same sequence of spots and MUs. Similarly, the four 4-paint repainting blocks 34 are identical while the eight 8-paint repainting blocks 36 are identical. Also, the sixteen 16-paint repainting blocks 38 are identical. Spots with $<2MU_{min}$ monitor units may not be repainted. They are divided into 1-paint repainting blocks 30, where odd numbered or designated spots are sorted into block 1a and even numbered or designated spots are sorted into block 1b.

Thereafter, taking into account of the repainting of spots of a layer, a scan mode is selected from a set of scan modes (FIG. 7) of different scan durations and implemented on the sorted spots (FIG. 6) of the layer until a particular scan mode is found that slows down the scanning of the spots of the layer to provide the layer with a treatment delivery time of duration greater than the period T=4 s of the breathing cycle. Accordingly, the treatment delivery time of the layer is step-wise increased by going from a fastest scan mode to slower and slower scan modes until the treatment delivery time of the layer exceeds the period T=4 s of the breathing cycle.

FIG. 7 shows a table 40 with eight scan modes in order of increasingly slower scan duration according to an embodiment. Each scan mode has a different scan path strategy. The scan duration increases with the number of the scan mode because the overall waiting time $t_{wait}$ of the layer increases. The scan mode that increases the treatment delivery time of the layer to more than the period T=4 s of the breathing cycle is selected. Scan mode 7 allows any even number of repaintings. For example, a spot with 40 repaintings will be placed twice in the 16-paint repainting blocks 38 and will be placed once in the 8-paint repainting blocks 36 because 40=16+16+8.

Figure 8:
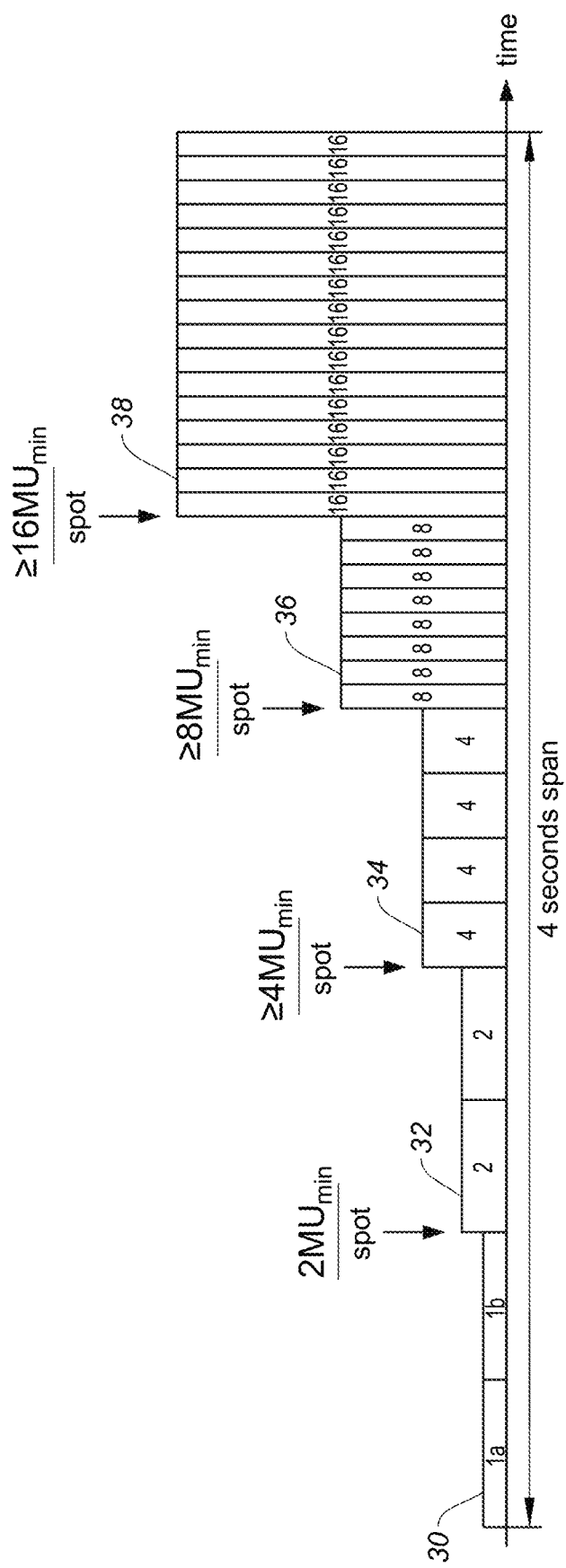
FIG. 8 depicts obtaining the treatment delivery time of a layer with a duration of 4 s (the period T=4 s of the breathing cycle) according to an embodiment.

Continuing with implementation of the new scan technique, thresholds for repainting are trimmed to obtain 4 s (the period T=4 s of the breathing cycle) for the treatment delivery time of the layer. As discussed earlier, scan modes (FIG. 7) were used to increase the treatment delivery duration of the layer to a value greater than the period T=4 s of the breathing cycle. By increasing some of the thresholds for spots with 4-paint, 8-paint, or 16-paint repaintings, the treatment delivery duration of the layer is shortened to the period T=4 s of the breathing cycle. For example, some of the spots that could be painted 8 times are instead painted 4 times, eliminating four waiting times $t_{wait}$. The threshold for 2 paintings remains at $2MU_{min}$, which ensures that any spot that may be painted twice or more is painted at least twice. FIG. 8 depicts obtaining the treatment delivery time of a layer with a duration of 4 s (the period T=4 s of the breathing cycle) according to an embodiment.

Figure 9:
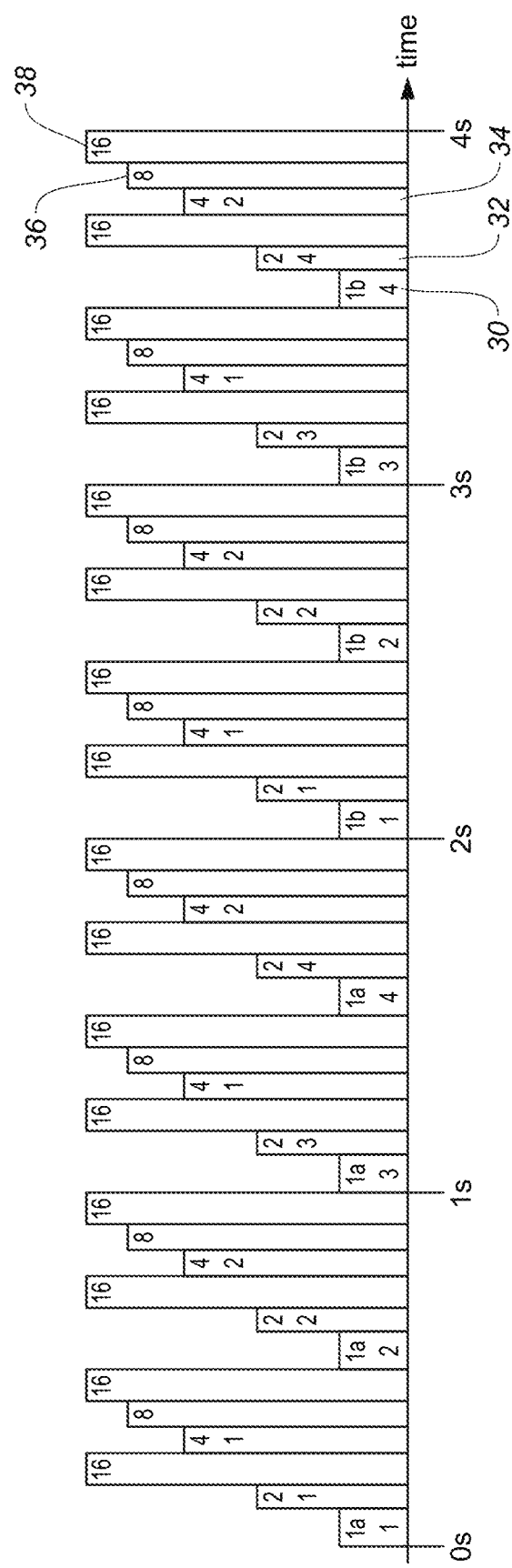
FIG. 9 illustrates repainting blocks rearranged according to an embodiment.

Next, the repainting blocks (or groups) 30, 32, 34, 36, and 38 are rearranged as illustrated in FIG. 9 according to an embodiment. The rearrangement provides the new scan technique with a quasi-periodic repainting scheme with a 0.5 s repetition rate and temporally spread-out repaintings of the spots of a layer throughout the duration of the period T=4 s of the breathing cycle no matter if the spots are painted twice, 4 times, 8 times, or 16 times. In an embodiment, the repaintings of the spots of a layer are evenly distributed throughout the duration of the period T=4 s of the breathing cycle. The spots that may be painted once are divided into the repainting blocks 30, where block 1a includes odd spots and block 1b includes even spots. The spots in these repainting blocks 30 (e.g., the n'th spot in block 1a and the n'th spot in block 1b) will often be neighboring spots. The new scan technique with the quasi-periodic repainting scheme shown in FIG. 9 ensures that these neighboring spots are visited with 2 seconds in between, which will tend to locally smear out the interplay effect even for these low-MU spots that may be painted once but not repainted.

Referring again to FIG. 9, the 2-paint repainting blocks 32 are divided into four quarters (2.1, 2.2, 2.3, 2.4) that are visited with 2 seconds in between. The 4-paint repainting blocks 34 are divided into two halves (4.1, 4.2) that are visited with 1 second in between. The 1-paint repainting blocks 30 are divided into quarters (1.a1, 1.a2, 1.a3, 1.a4, 1.b1, 1.b2, 1.b3, 1.b4), where neighboring odd and even spots are visited with 2 seconds in between.

Figure 10:
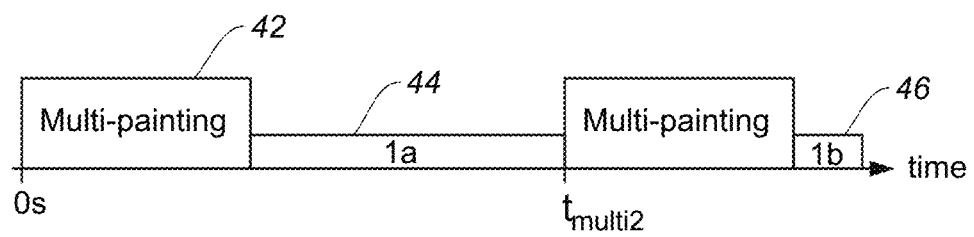
FIG. 10 shows new scan technique with repainting scheme for a special case according to an embodiment.

Some layers have too few spots with too few MUs to allow the treatment delivery duration of the layer to be extended beyond the period T=4 s of the breathing cycle by the scan modes 1-7 of FIG. 7. In such cases, the new scan technique with the repainting scheme shown in FIG. 10 is used as an alternative according to an embodiment. As indicated in FIG. 7, the scan modes 8a and 8b allow any number of repaintings (both even and odd numbers). Scan modes 8a and 8b are identical except that they are applicable for layers with duration equal to and smaller than the period T=4 s of the breathing cycle, respectively. Accordingly, the treatment delivery duration of the layer may be further increased at the cost of less evenly spread-out repaintings.

Referring again to FIG. 10, the alternative available is used when the new scan technique with the quasi-periodic repainting scheme of FIGS. 8 and 9 fails to increase the treatment delivery duration of the layer beyond the period T=4 s of the breathing cycle because the layer has too few spots and MUs. As depicted in FIG. 10, the two multi-paint repainting blocks 42 are identical and may include any number of paintings for a spot. The 1-paint repainting blocks 44 and 46 (1a and 1b) may include spots that are painted once as well as spots that are painted an odd number of times (n>3) and therefore also are placed in the multi-paint repainting blocks 42. The 1-paint repainting blocks 44 and 46 are split into block 1a and block 1b in order to get the $time_{multi}$ between the multi-paint repainting blocks 42 as close to half the period T/2=2 s of the breathing cycle as possible, which will reduce the interplay effect for spots in the multi-paint repainting blocks 42.

Some layers with a very high number of spots and MU may have a treatment delivery duration that exceeds the period T=4 s of the breathing cycle even with the slowest scan mode of FIG. 7. For these layers, a treatment delivery duration of twice the period T2=8 s of the breathing cycle covering two breathing cycles may be obtained in a similar manner as described above. For example, the new scan technique with the quasi-periodic repainting scheme similar to FIG. 9 may be obtained for each of the two breathing cycles. Moreover, the spot scan pattern may be reversed for the first breathing cycle relative to the second breathing cycle in order to further smear out any residual interplay effect.

Figure 11:
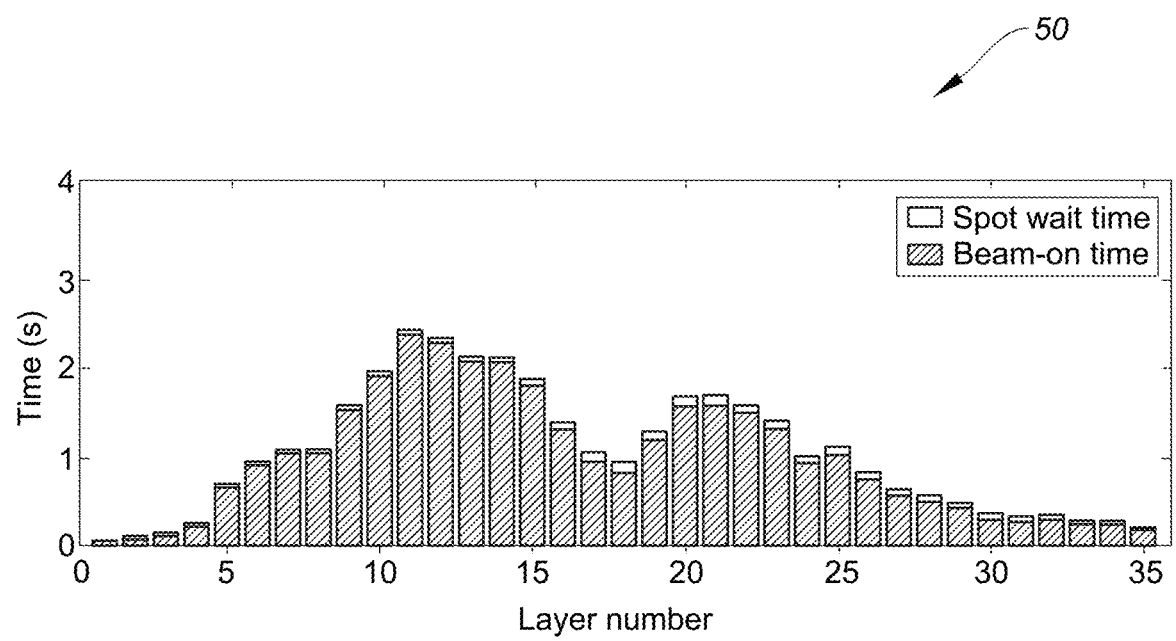
FIG. 11 shows a graph with examples of the treatment delivery durations of layers for one field with a planned treatment delivery without use of the new scan technique.
Figure 12:
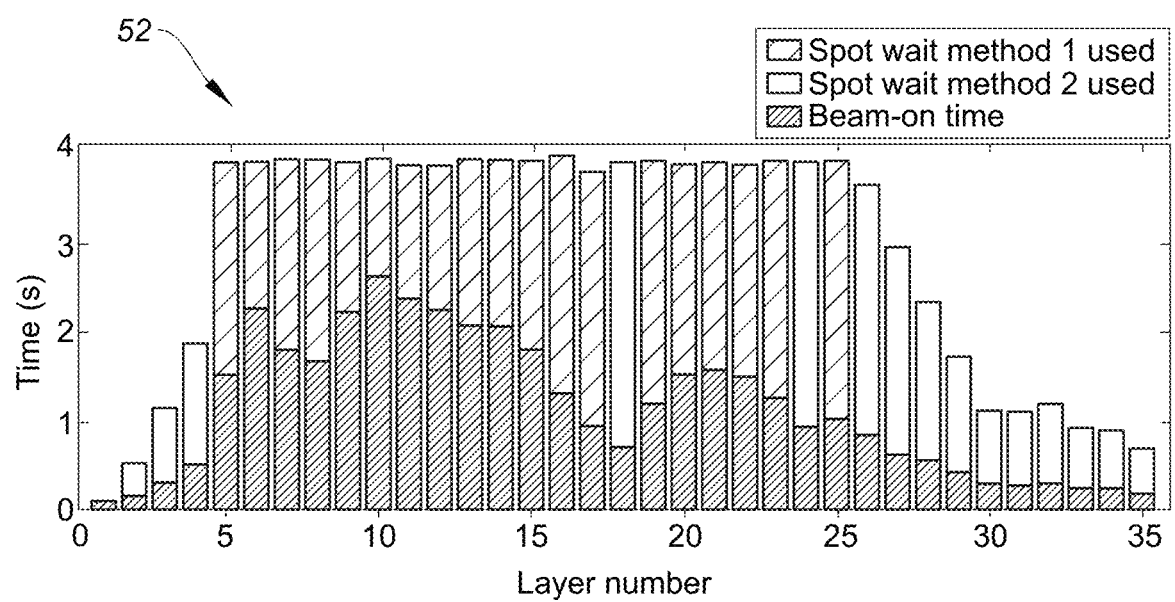
FIG. 12 illustrates a graph with examples of the treatment delivery durations of layers for one field with treatment delivery according FIGS. 9 (method 1) and 10 (method 2) according to an embodiment.
Figure 13:
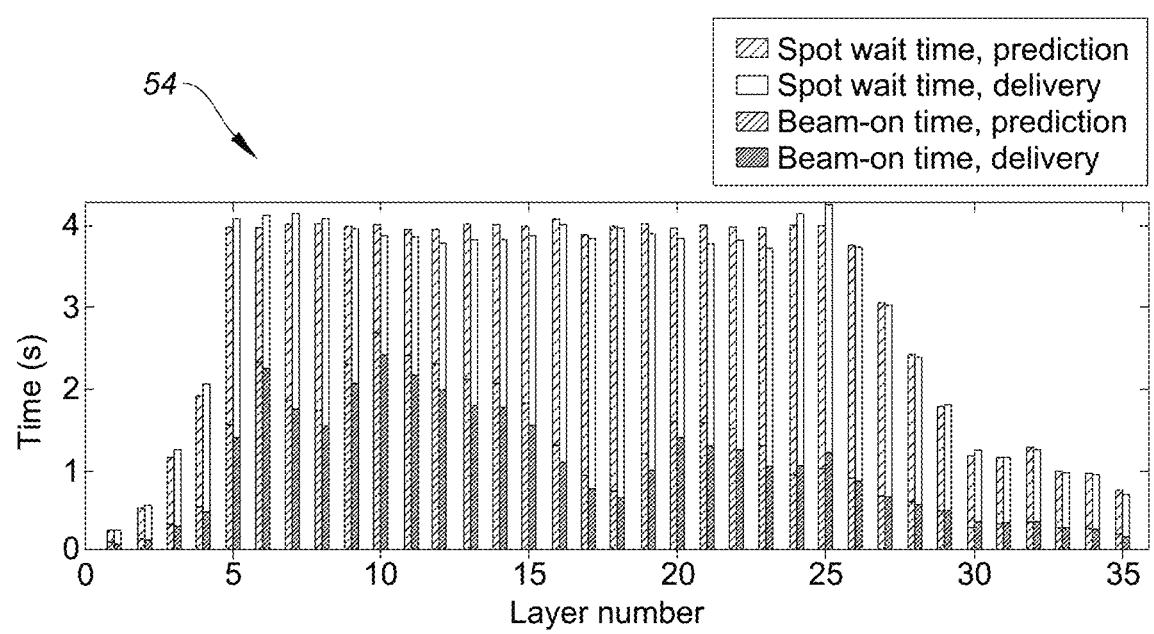
FIG. 13 depicts a graph that demonstrates actual treatment delivery times are reasonably close to predicted treatment delivery times with equations (1)-(3) of FIG. 2B according to an embodiment.

The new scan technique that integrates repainting was investigated for 13 clinical proton PBS fields. For each field, the treatment delivery of each layer was rearranged as shown in FIGS. 8, 9, and 10. FIG. 11 shows a graph 50 with examples of the treatment delivery durations of layers for one field with a planned treatment delivery without use of the new scan technique while FIG. 12 illustrates a graph 52 with examples of the treatment delivery durations of layers for one field with treatment delivery according FIGS. 9 (method 1) and 10 (method 2) according to an embodiment, where the times are calculated with equations (1)-(3) of FIG. 2B. As shown in FIG. 13, the graph 54 demonstrates that the actual treatment delivery times recorded in log files for 35 layers under the new scan technique are reasonably close to the predicted treatment delivery times with equations (1)-(3) of FIG. 2B according to an embodiment.

Continuing, the treatment plans of five patients treated with proton PBS for thoracic and abdominal tumors were used for experimental dosimetric evaluation of the new scan technique. The five plans were two- or three-field plans with single-field-optimization in the treatment planning system and fraction doses between 1.8 Gy and 4.5 Gy. The tumors were pancreas, liver, lung/bronchus neoplasm, a non-small cell lung cancer tumor in right lower lobe, and a renal cell carcinoma. The plans represent a wide range of tumor sites, volumes, and doses. The five evaluation proton PBS plans had a total of 12 fields with 237 energy layers. The last two columns in FIG. 7 show the percentage of layers and MUs for each of the eight scan modes. As depicted in FIG. 7, all eight scan modes were used. Although 33.8% of the layers were scanned with the sub-optimal scan mode 8b with <4 s treatment delivery duration, these layers only constituted 6.5% of the total dose (or MU) as seen in the bottom row of FIG. 7. The layers with less than 4 s treatment delivery duration were often the most deep and shallow layers (first and last layers in the field) as in the examples in FIGS. 11-13. Further, 4.6% of the layers (2.3% of the dose or MU) were delivered with scan mode 8a with treatment delivery duration equal to 4 s, but with repaintings that were less uniformly distributed throughout the breathing cycle than for scan modes 1-7.

Figure 14:
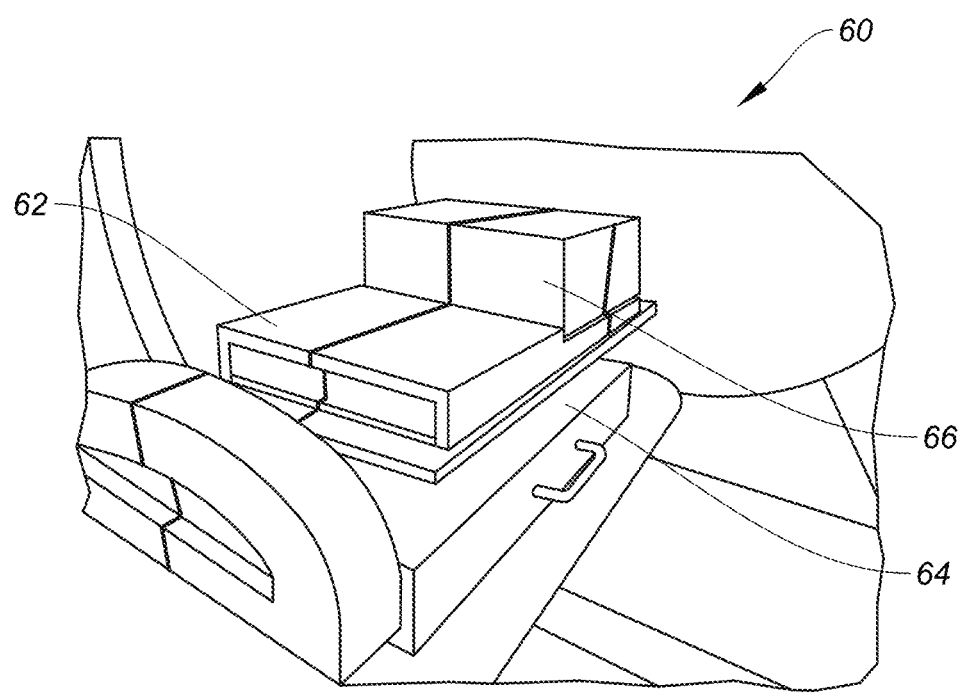
FIG. 14 illustrates a set-up to investigate the new scan technique according to an embodiment.

The ability to mitigate the interplay effect of the new scan technique was investigated with a set-up illustrated in FIG. 14 according to an embodiment. Each of the 12 proton PBS fields were delivered to an ion chamber array 62 carried by a motion stage 64. The ion chamber array 62 measured the 2D dose distribution with a frame rate of 0.1 s. Blocks of solid water 66 on the ion chamber array 62 gave a measuring depth corresponding to a proximal end of the spread-out Bragg peak. Each field was delivered three times to the ion chamber array 62: Once without motion and twice with a 4 s period, 3 cm peak-to-peak, sinusoidal motion, where the treatment delivery was started at two different times relative to the motion cycle. For comparison, similar static+2× motion experiments were also performed (1) with the original default scan mode (without any repainting) and (2) with up to 8 times repaintings. In the latter case, all spots with >8$MU_{min}$ were painted 8 times, while spots that could only be painted N times (N<8) received N painting during the first N passes of the spot map. In total, 108 treatment deliveries were performed (12 fields×3 repainting schemes×3 motion cases).

Figure 15:
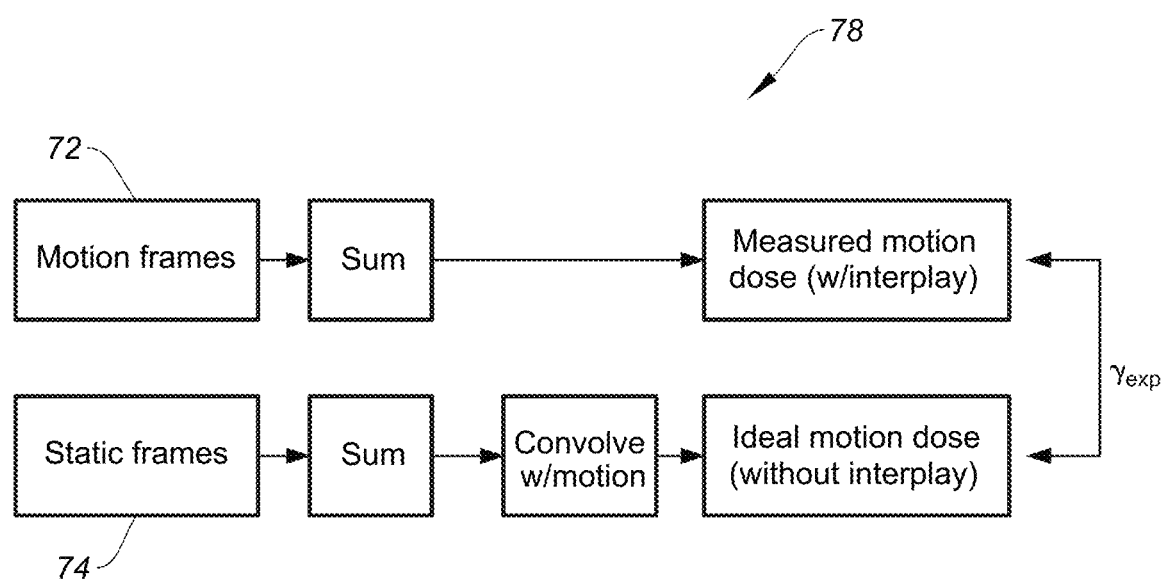
FIG. 15 shows a block diagram for performing a gamma test according to an embodiment.

For each motion experiment, the time resolved dose frames were summed in order to obtain the accumulated motion dose with the interplay effect as demonstrated in the upper row 72 of the block diagram 78 of FIG. 15. This dose was then compared with a reference dose, which was the accumulated static dose smeared or convolved with the known sinusoidal phantom motion as demonstrated in the lower row 74 of the block diagram 78 of FIG. 15. This reference dose represents an ideal motion dose distribution that is blurred due to motion, but otherwise without any interplay effect. The comparison with this reference dose was performed as a gamma test, where the percentage of ion chamber measurements fulfilling the 3%/3 mm gamma pass criterion was reported. Ion chamber measurements with less than 10% of the maximum dose in the reference dose map were excluded in the gamma test.

Figure 16:
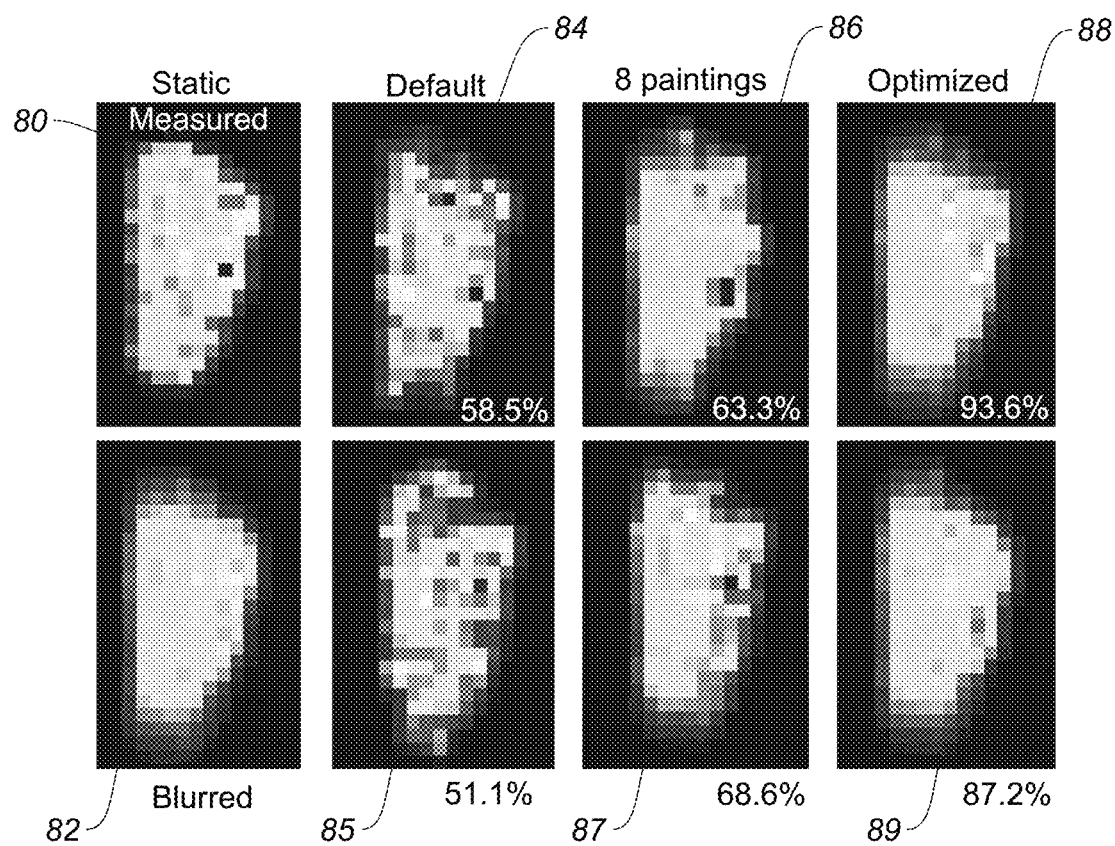
FIG. 16 depicts examples of measured doses with an ion chamber array for a patient under treatment according to an embodiment.

FIG. 16 depicts examples of measured doses with an ion chamber array for a patient under treatment according to an embodiment. Illustrated are a static dose (measured) 80, a static dose (blurred) 82 convolved with the applied 3 cm peak-to-peak sinusoidal motion, i.e. the ideal smeared-out interplay-effect-free dose distribution. The three right columns show measured motion doses with the default delivery (no repainting) 84 and 85, conventional 8-repainting delivery 86 and 87, and treatment delivery according to the new scan technique 88 and 89 in experiments with the treatment starting in cranial phantom position (upper row) and caudal phantom position (lower row). The listed numbers specify the 3%/3 mm gamma pass rate of the motion doses when compared with the ideal blurred static dose (i.e., compared with the static dose (blurred) 82). The treatment delivery according to the new scan technique 88 and 89 had (1) considerably higher gamma pass rates (i.e., lower interplay effect) and (2) considerably less variations when comparing one motion experiment with another.

The results for 3×24 motion experiments are summarized in FIG. 17 according to an embodiment, showing a clear and highly significant improvement with the treatment delivery according to the new scan technique. Mean (±1 standard deviation) of the 3%/3 mm gamma pass rate in motion experiments with treatment delivered with the default scheme (upper row), with 8 repaintings (middle row), and with the new scan technique (lower row) when compared with a blurred static reference dose. Further, experimental results, simulations of the experiments, and simulations extended from 1 to 10 starting phases for each motion experiment are demonstrated in FIG. 17.

Continuing, a series of simulations were performed in order to expand the scope of the investigation of the new scan technique beyond what is practically feasible with experiments. The measured motion doses were reproduced from the measured static doses.

Figure 18:
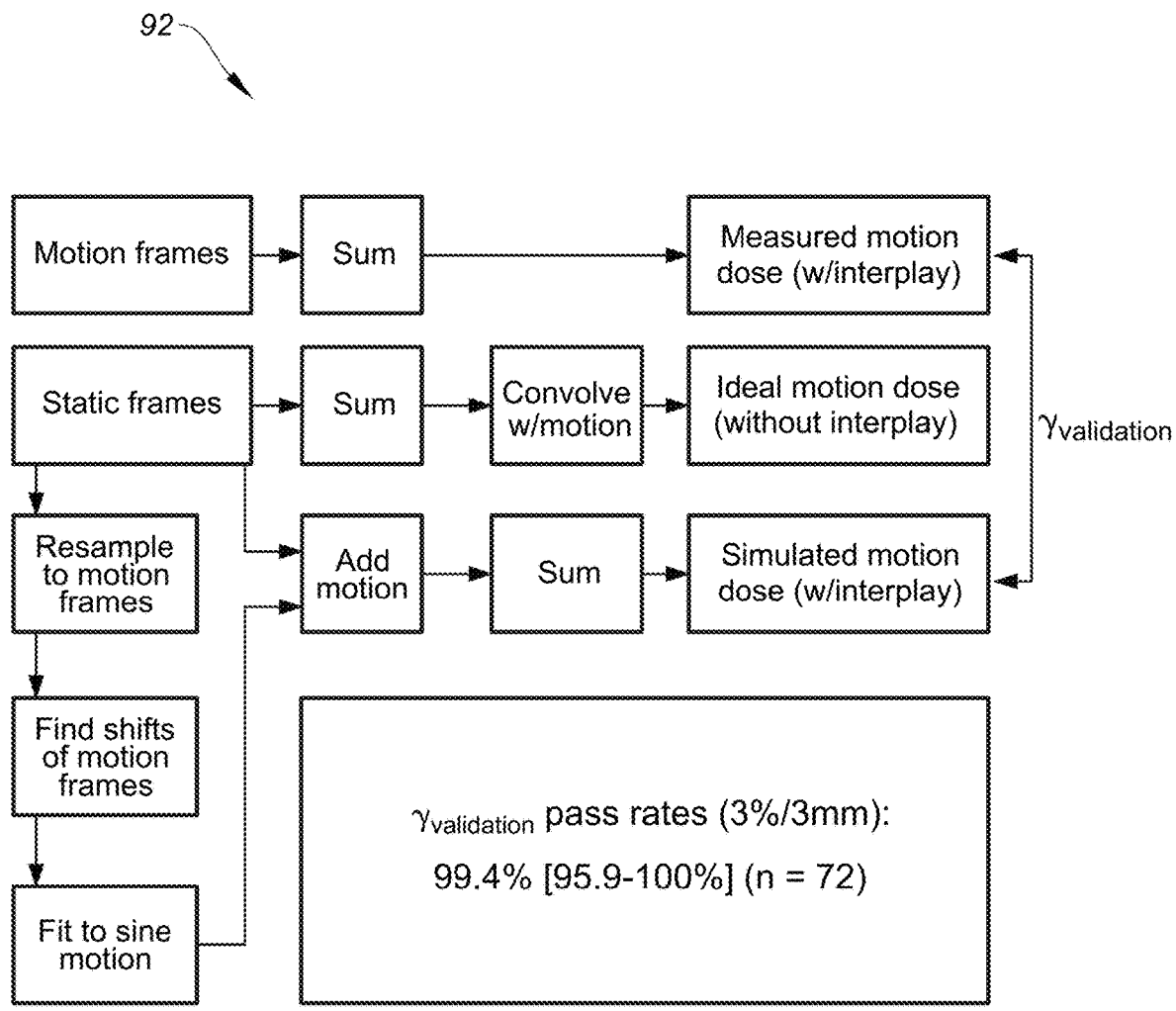
FIG. 18 shows a block diagram for a gamma test according to an embodiment.

For each of the 72 motion experiments, the time resolved 2D dose frames of the corresponding static experiment were first resampled to obtain the same number of dose frames for each energy layer as in the motion experiment as depicted in the block diagram 92 of FIG. 18 according to an embodiment. Next, the shift of each frame in the motion experiment (i.e., the position of the motion stage at the moment of frame exposure) was determined as the shift that gave the highest normalized cross correlation with the corresponding frame in the static experiment. Finally, the shifts of all motion frames were fitted to the known 3 cm, 4 s period sinusoidal motion. As result of this procedure, the phantom position for all dose frames in the motion experiment was now known. This information was used to simulate the motion dose from the static dose by adding the known motion to each frame and summing up the frames as shown in FIG. 18 (Simulated motion dose). The agreement between simulated and measured doses was very high with a mean 3%/3 mm gamma pass rate of 99.4%. It shows that the static-measurement-based simulations can reproduce the motion doses with high accuracy.

Figure 19:
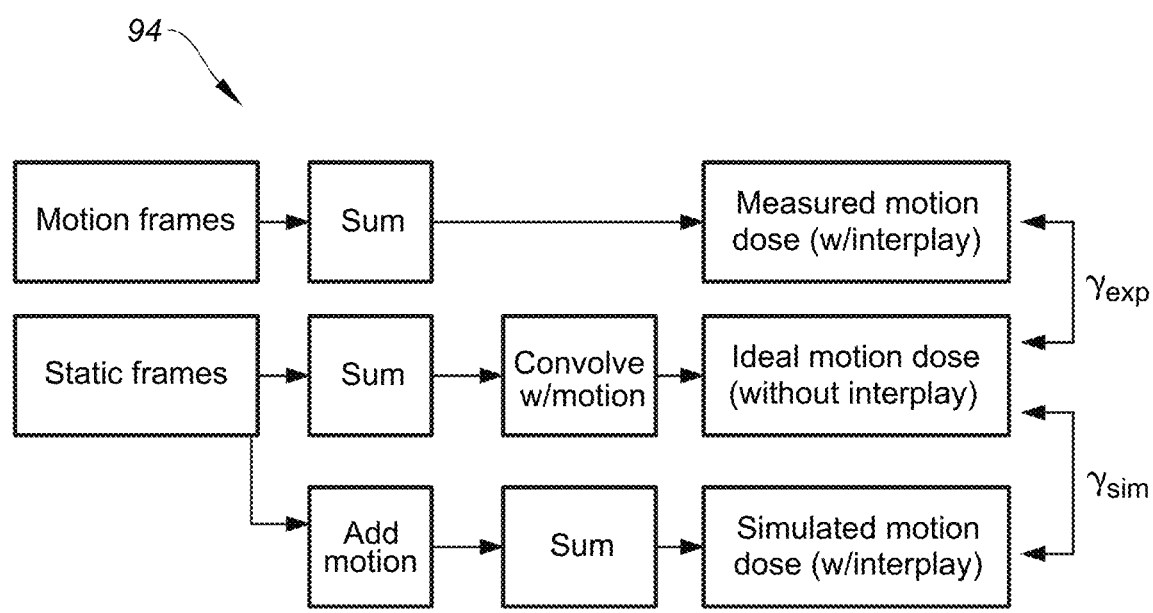
FIG. 19 depicts a block diagram to reproduce experimental gamma pass rates for the interplay effect according to an embodiment.
Figure 20:
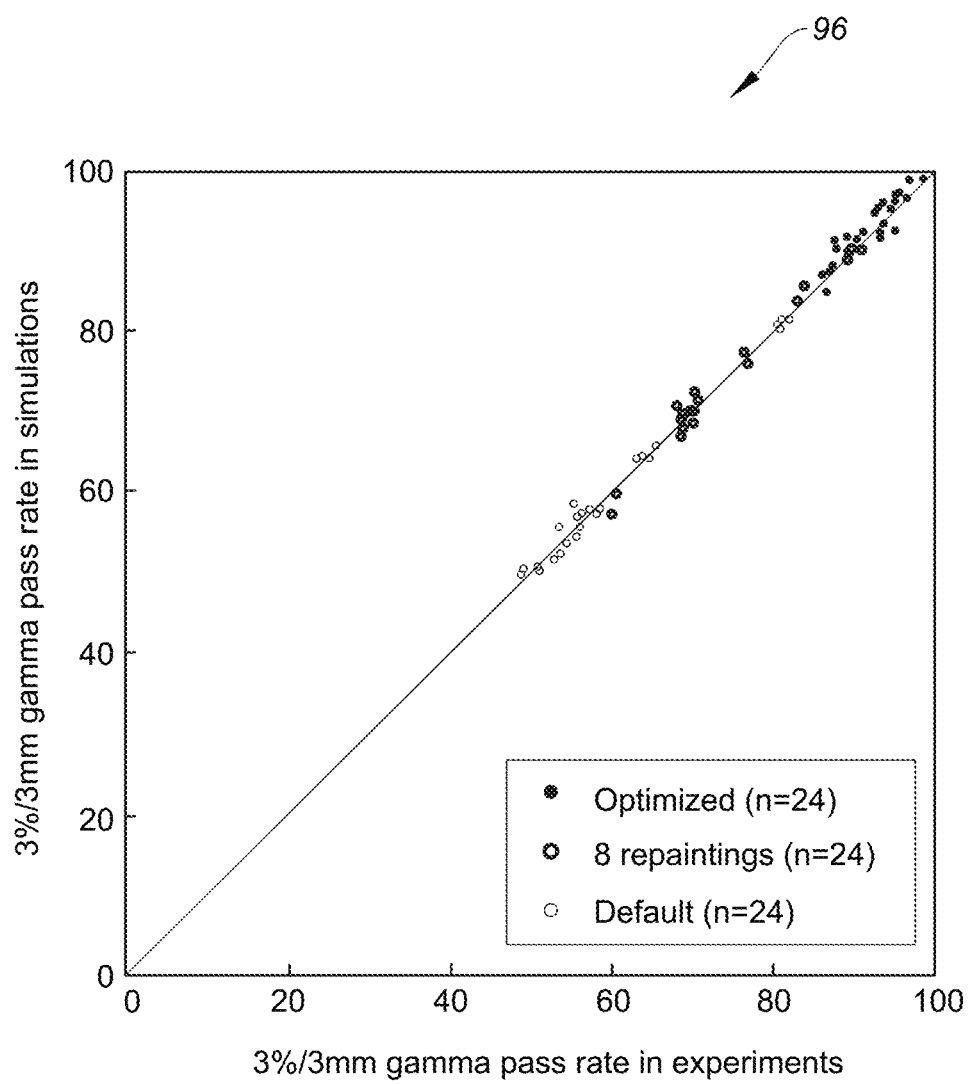
FIG. 20 illustrates a graph of gamma pass rates according to an embodiment.

Next, the ability of the simulations to reproduce the experimental gamma pass rates for the interplay effect was investigated as indicated with the block diagram 94 of FIG. 19 according to an embodiment. As shown in the graph 96 of FIG. 20 according to an embodiment, the simulations accurately reproduced the experimental 3%/3 mm gamma pass rates with a root-mean-square error of 1.3 percent-spot. This is also shown in FIG. 17 (compare first and second columns).

Figure 21:
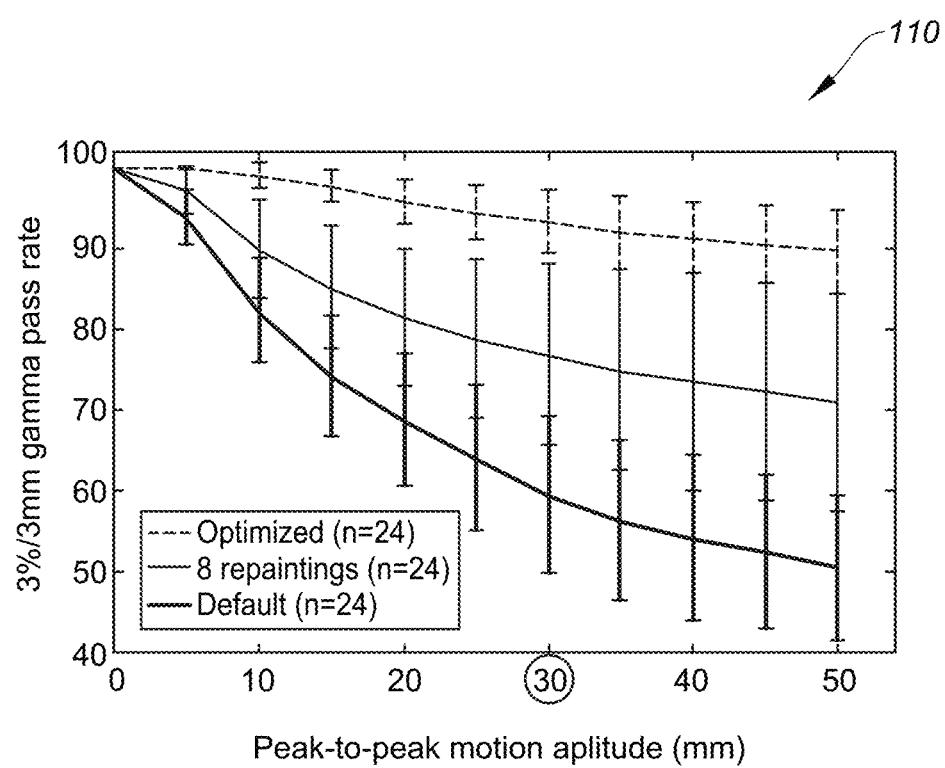
FIG. 21 shows a graph for investigating the impact of motion amplitude according to an embodiment.

Simulations were used to investigate the impact of the motion amplitude as shown in the graph 110 of FIG. 21 according to an embodiment. The new scan technique (optimized) largely reduced the interplay effect even with very large motion of 50 mm. The mean gamma pass rate with 50 mm motion for the new scan technique (optimized) was better than the mean gamma pass rate of 8 repaintings with only 10 mm motion.

Figure 22:
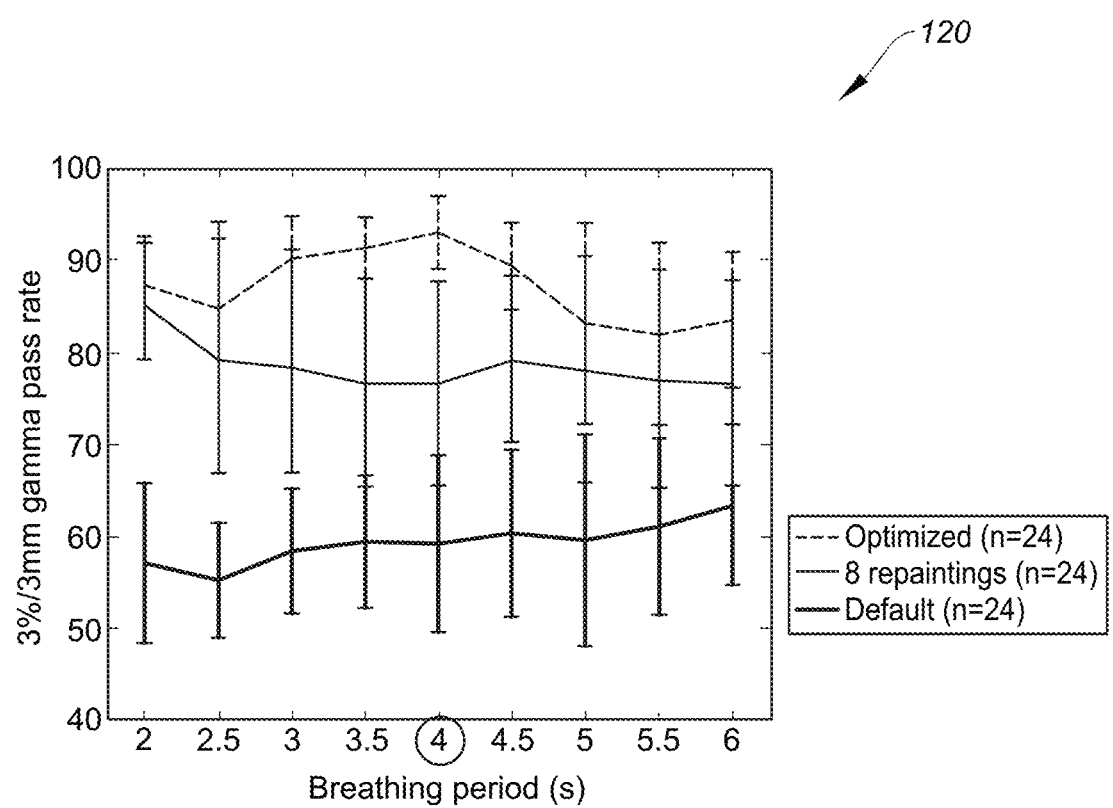
FIG. 22 shows a graph for investigating the impact of a breathing period differing from period T=4 s according to an embodiment.

Further, the impact of a breathing period differing from period T=4 s was investigated as shown in the graph 120 of FIG. 22 according to an embodiment. It is relevant to know how much the interplay effect mitigation of the new scan technique (optimized) degrades if the patient happens to have another breathing period at treatment than the one used for plan delivery optimization (period T=4 s). Although the interplay mitigation of the new scan technique (optimized) decreased with other motion periods, the mean gamma pass rate stayed above 85% for a wide range of breathing periods.

Figure 23:
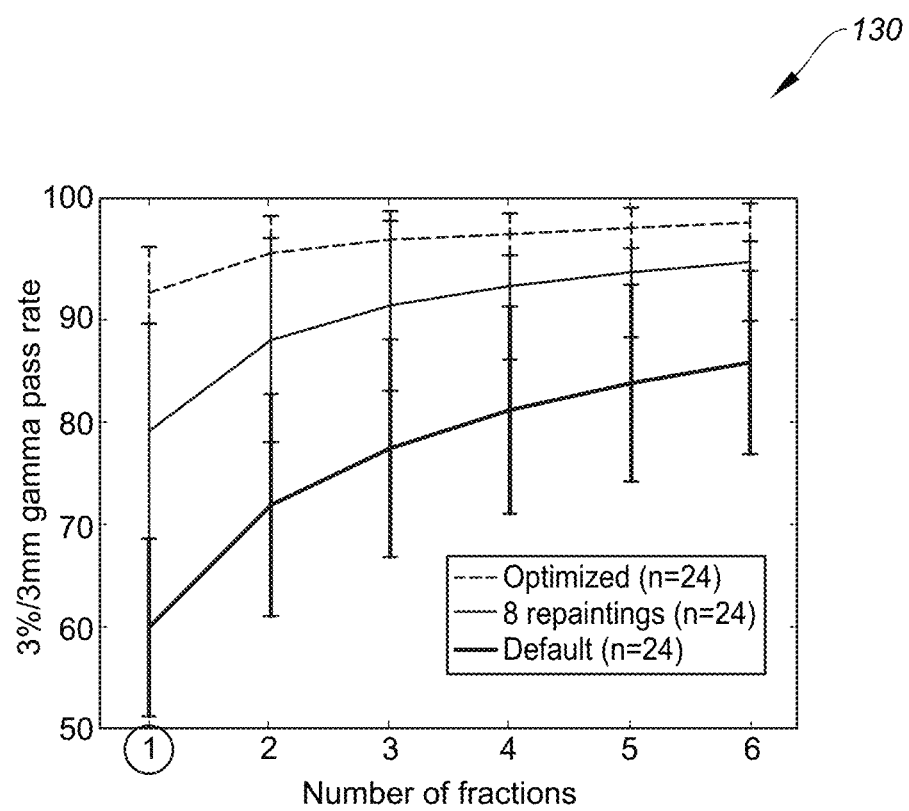
FIG. 23 shows a graph for investigating the smearing of the interplay effect with fractionated delivery according to an embodiment.

The smearing of the interplay effect with fractionated delivery was investigated as shown in the graph 130 of FIG. 23 according to an embodiment by simulating all possible combinations of 10 motion starting phases at N fractions (N=1-6) for all 72 motion experiments. The mean and standard deviation of the 3%/3 mm gamma pass rate were calculated for all $10^N$ possible combinations of N-fraction treatment courses for each motion experiment. The results are shown in FIG. 23. The new scan technique (optimized) was clearly superior with a mean gamma pass rate after a single fraction (92.5%) that was equal to the mean gamma pass rate of 8 repaintings after 3.5 fractions, but with a much smaller standard deviation (error bars in FIG. 23). The standard deviation was 4.6% after only 1 fraction delivered with the new scan technique (optimized) while it was still 5.7% after 6 fractions with 8 repaintings. It indicates the absence of outliers with large interplay effects for the new scan technique (optimized).

Figure 24:
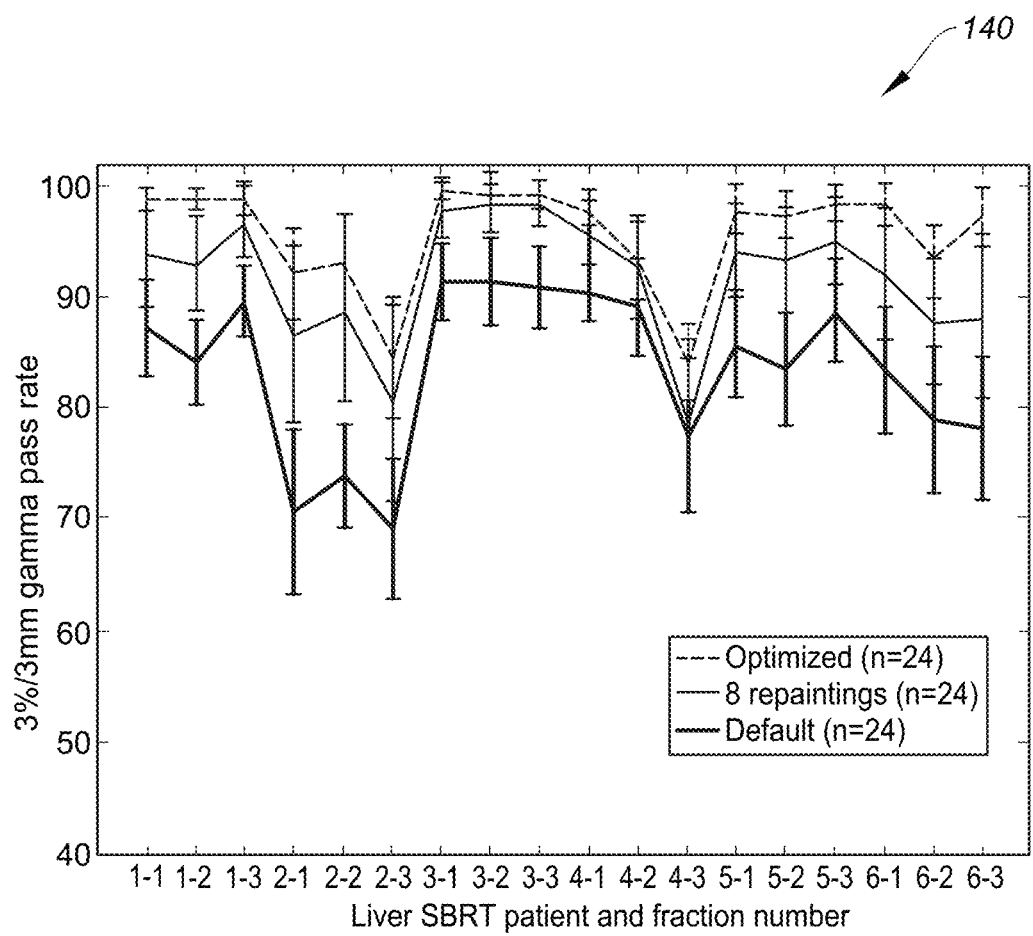
FIG. 24 depicts a graph for investigating the interplay effect for the actually measured tumor motion as measured for six liver SBRT patients during treatment delivery with kilovoltage intrafraction imaging (KIM) according to an embodiment.

Continuing, the interplay effect was investigated for the actually measured tumor motion as measured for six liver SBRT patients during treatment delivery with kilovoltage intrafraction imaging (KIM) as shown in the graph 140 of FIG. 24 according to an embodiment. The results are shown in FIG. 24 for the measured motion at all fractions (6 patients×3fractions/patient). Unlike the sinusoidal motion studied so far, the patient-measured motion trajectories have many irregularities such as variations in waveform, period, and amplitude from cycle to cycle as well as baseline shifts. Although the new scan technique (optimized) was superior to 8 repaintings (and no repaintings) for all fractions, the gamma pass rate was somewhat low for Patients 2 and 4, who had very fast breathing periods of less than 3 seconds. The new scan technique (optimized) designed for this fast breathing would perform better than the current implementation aimed for period T=4 s for treatment delivery duration per energy layer.

Figure 25:
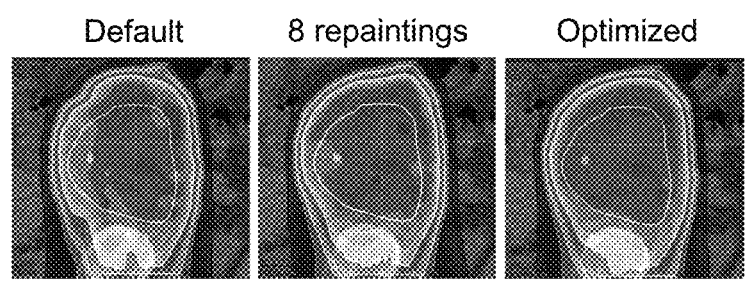
FIG. 25 illustrates three dose distributions according to an embodiment.

As a final investigation of the interplay effect mitigation, delivery of all three proton PBS fields for the first patient in the study was simulated in a Matlab program with the three delivery schemes (optimized, 8 repaintings, default). The Matlab program distributed all spots in ten different breathing phases and generated a DICOM plan file for each breathing phase. A layer shift time of 1.1 seconds, a spot delivery time according to equations (1)-(3) of FIG. 2B, and a breathing period T=4 s were assumed. The ten DICOM plans were imported into the ten phases of a 4DCT scan for the patient in a treatment planning system. The phase-specific dose was calculated in each 4DCT phase and summed in the full exhale phase using deformable image registration. As shown in FIG. 25, the new scan technique (optimized) gave a superior dose distribution with fewer interplay effects according to an embodiment.

Figure 26:
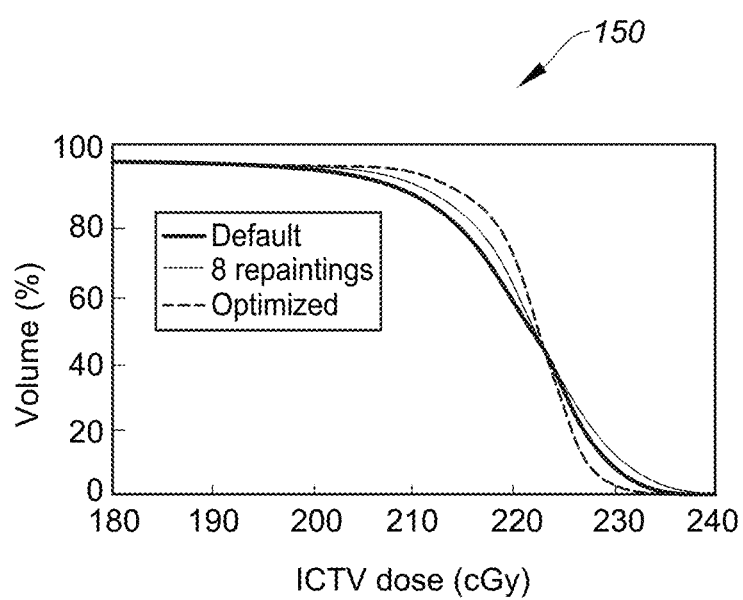
FIG. 26 shows a dose-volume histogram for internal clinical target volume (ICTV) of 4D dose reconstruction according to an embodiment.

FIG. 26 depicts a dose-volume histogram 150 for the internal clinical target volume (ICTV) of 4D dose reconstruction in a treatment planning system with the default delivery, with 8 repaintings, and with the new scan technique (optimized) for the first patient (pancreas) according to an embodiment. The new scan technique (optimized) leads to a more uniform target dose with fewer interplay effects.

The new scan technique may be implemented in many ways, notably as software running on a PC or similar. The presently disclosure further relates to a system for mitigating interplay effects in particle radiation therapy comprising a non-transitive, computer-readable storage device for storing instructions that performs a method for mitigating interplay effects in particle radiation therapy. The disclosure further relates to a computer program having instructions which when executed by a computing device or system causes the computing device or system to mitigate interplay effects in particle radiation therapy. Computer program should be construed broadly and include programs to be run on a PC, a part of the computer system facilities in a particle radiation therapy center, or software designed to run on smartphones, tablet computers or other mobile devices. Computer programs and mobile applications include software that is free and software that has to be bought, and also include software that is distributed over distribution software platforms.

The present disclosure further relates to a particle therapy system comprising a particle beam generator for creating a particle beam used for particle radiation therapy, a beam transfer unit for delivering the particle radiation therapy to a target, a beam scanning unit configured to scan the particle beam across the target, and a processing unit configured to generate a scan pattern for the beam scanning unit by means described above to mitigate interplay effect of the particle radiation therapy. The particle therapy system may for example be a part of a proton center with one or more cyclotron accelerators. In a further embodiment, the present disclosure relates to a method for treatment of a cancer tumor in a region of a patient under periodic movement by submitting a target volume of the tumor to particle radiation therapy. In still another embodiment, the period of movement of the cancer tumor is obtained. The target volume is divided into a plurality of layers. Each of the layers is divided into a plurality of spots. A planned dose of particle radiation therapy of each spot of the target volume is calculated. A scan pattern is generated by means of the herein disclosed. The particle radiation therapy is delivered to the target volume (e.g., a tumor) according to the scan pattern to mitigate interplay effect of the particle radiation therapy. The cancer tumor (or several of them) may for example be located in the abdominal or the thoracic regions of the patient. But, cancer tumors in other anatomical regions may also be relevant, in particular if they are under influence of periodic movements during the particle radiation therapy.

The foregoing descriptions of specific embodiments have been presented for purposes of illustration and description. They are not intended to be exhaustive or to limit the disclosure to the precise forms disclosed, and many modifications and variations are possible in light of the above teaching. The embodiments were chosen and described in order to best explain the principles of the disclosure and its practical application, to thereby enable others skilled in the art to best utilize the disclosure and various embodiments with various modifications as are suited to the particular use contemplated. It is intended that the scope of the disclosure be defined by the Claims appended hereto and their equivalents.

What is claimed is:

1. A method of mitigating interplay effect in particle radiation therapy for delivery to a moving target including a period of movement, the particle radiation therapy defining a planned dose in each spot of each layer of the moving target, the method comprising:
dividing the planned dose in each spot into a number of spot repaintings; and
generating a scan pattern for each layer by
defining a beam-on time at each spot for each spot repainting, and
calculating a wait time between consecutive beam-on times to distribute the spot repaintings for each spot of a respective layer over a duration of an integer number of periods of movement.

2. The method according to claim 1, wherein the number of spot repaintings at each spot is maximized according to a predefined minimum dose per spot of the particle radiation therapy.

3. The method according to claim 1, wherein the spot repaintings of each spot of a layer are distributed evenly over the duration of the integer number of periods of movement.

4. The method according to claim 1, wherein the number of spot repaintings for each spot is sorted into blocks, wherein the number of spot repaintings in each block is an integer power of two.

5. The method according to claim 4, wherein the spot repaintings of each block are distributed evenly over an integer number of periods of movement.

6. The method according to claim 1, wherein the spot repaintings in the scan pattern are distributed by adjusting a sequence order of spots and/or spot repaintings in a layer and/or the wait time between consecutive beam-on times in a layer.

7. The method according to claim 1, wherein the wait time between consecutive beam-on times in a layer is adjusted by selecting a beam pause before one or more spots in the scan pattern.

8. The method according to claim 1, wherein particles for the particle radiation therapy are from the group of: protons, ions, neutrons, and electrons.

9. The method according to claim 1, wherein the particle radiation therapy is conducted using pencil beam scanning.

10. The method according to claim 1, wherein the moving target comprises a tumor or at least part thereof.

11. The method according to claim 1, wherein the period of movement is due to breathing and/or heartbeat of a patient comprising the moving target.

12. The method according to claim 11, wherein the breathing and/or heartbeat movement includes a breathing and/or heartbeat period and is determined with four-dimensional computed tomography.

13. The method according to claim 1, further comprising: assisting synchronization of breathing of a patient and the period of movement.

14. The method according to claim 13, wherein the patient is assisted by audio and/or visual guidance.

15. The method according to claim 1, wherein the scan pattern is generated such that spot repaintings of spots in a layer that are irradiated once are distributed such that a first group of the spots are irradiated during a first part of the period of the periodic movement and a second group of the spots are irradiated during a second part of the period of the movement.

16. The method according to claim 1, wherein the scan pattern is generated such that layers with scan times of two periods are scanned such that repainting blocks of two or more spot repaintings are separated into two identical scan patterns, wherein a first scan pattern is performed in a first period of two periods and a second scan pattern is performed in a second period of two periods.

17. The method according to claim 1, wherein the scan pattern is generated such that layers with scan times of two periods are scanned such that repainting blocks of two or more spot repaintings are separated into two scan patterns, wherein a first scan pattern is performed in a first period and a second scan is performed in a second period, and wherein the second scan pattern is the reverse of the first scan pattern.

18. The method according to claim 1, wherein the scan pattern is generated such that layers with a scan time duration less than the period of the movement are scanned using a pattern with a maximum scan time duration.

19. The method according to claim 1, wherein the method is computer implemented.

20. A method for treatment of a cancer tumor in a region of a patient under periodic movement by submitting a target volume of the tumor to particle radiation therapy, the method comprising:
obtaining a period of movement of the cancer tumor;
dividing the target volume into a plurality of layers and dividing each of the layers into a plurality of spots;
calculating a planned dose of the particle radiation therapy of each spot of the target volume and dividing the planned dose in each spot of each layer into a number of spot repaintings;
generating a scan pattern for each layer by defining a beam-on time at each spot for each spot repainting and calculating a wait time between consecutive beam-on times to distribute the spot repaintings for each spot of a respective layer over a duration of an integer number of periods of movement; and
delivering the particle radiation therapy to the target volume according to the scan pattern to mitigate interplay effect of the particle radiation therapy.

21. A particle radiation therapy system comprising:
a particle beam generator operable to create a particle beam used for particle radiation therapy;
a beam transfer unit operable to deliver the particle radiation therapy to a target;
a beam scanning unit configured to scan the particle beam across a plurality of layers of the target, wherein each layer includes a plurality of spots, and
a processing unit configured to generate a scan pattern for each layer for the beam scanning unit by defining a beam-on time at each spot for each spot repainting and calculating a wait time between consecutive beam-on times to distribute the spot repaintings for each spot of a respective layer over a duration of an integer number of periods of movement to mitigate interplay effect of the particle radiation therapy.

* * * * *